United States Patent
Kerr

(10) Patent No.: US 10,105,209 B2
(45) Date of Patent: *Oct. 23, 2018

(54) STENT/GRAFT ASSEMBLY

(71) Applicant: Andrew Kerr, New York, NY (US)

(72) Inventor: Andrew Kerr, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/440,073

(22) Filed: Feb. 23, 2017

(65) Prior Publication Data

US 2017/0224468 A1 Aug. 10, 2017

Related U.S. Application Data

(60) Continuation of application No. 14/706,185, filed on May 7, 2015, which is a continuation of application
(Continued)

(51) Int. Cl.
| | | |
|---|---|---|
| *A61F 2/82* | (2013.01) | |
| *A61F 2/07* | (2013.01) | |
| *A61F 2/90* | (2013.01) | |
| *A61F 2/88* | (2006.01) | |
| *A61F 2/848* | (2013.01) | |

(Continued)

(52) U.S. Cl.
CPC .............. *A61F 2/07* (2013.01); *A61F 2/82* (2013.01); *A61F 2/848* (2013.01); *A61F 2/88* (2013.01); *A61F 2/89* (2013.01); *A61F 2/90* (2013.01); *A61F 2002/061* (2013.01); *A61F 2002/065* (2013.01); *A61F 2002/067* (2013.01); *A61F 2002/075* (2013.01); *A61F 2002/077* (2013.01); *A61F 2002/826* (2013.01); *A61F 2002/828* (2013.01); *A61F 2002/8483* (2013.01); *A61F 2002/8486* (2013.01); *A61F 2002/91558* (2013.01); *A61F 2002/91583* (2013.01); *A61F 2220/005* (2013.01); *A61F 2220/0016* (2013.01); *A61F 2220/0058* (2013.01); *A61F 2220/0075* (2013.01); *A61F 2220/0083* (2013.01)

(58) Field of Classification Search
CPC ................. A61F 2/07; A61F 2002/075; A61F 2002/91583; A61F 2002/91558
USPC ................................................ 623/1.13, 1.16
See application file for complete search history.

(56) References Cited

U.S. PATENT DOCUMENTS

| | | |
|---|---|---|
| 5,064,435 A | 11/1991 | Porter |
| 5,078,726 A | 1/1992 | Kreamer |

(Continued)

FOREIGN PATENT DOCUMENTS

| | | |
|---|---|---|
| EP | 0 732 089 | 9/1996 |
| EP | 0 809 980 | 12/1997 |

(Continued)

OTHER PUBLICATIONS

Fundamentals of Fixed Prosthodontics Third Edition—Chapter 9—Principles of Tooth Preparations—pp. 119-131.
(Continued)

*Primary Examiner* — David H Willse
*Assistant Examiner* — Javier Blanco
(74) *Attorney, Agent, or Firm* — Blank Rome LLP

(57) ABSTRACT

A stent/graft assembly includes a tubular graft connected in substantially end-to-end relationship with a generally tubular stent. Free ends of the stent and graft extend in opposite directions from the end-to-end connection during a pre-deployment orientation of the assembly.

9 Claims, 36 Drawing Sheets

Related U.S. Application Data

No. 13/933,522, filed on Jul. 2, 2013, now Pat. No. 9,050,182, which is a continuation of application No. 13/591,444, filed on Aug. 22, 2012, now abandoned, which is a continuation of application No. 12/844,073, filed on Jul. 27, 2010, now Pat. No. 8,257,423, which is a division of application No. 12/137,632, filed on Jun. 12, 2008, now abandoned, which is a division of application No. 10/849,652, filed on May 20, 2004, now abandoned, which is a continuation-in-part of application No. 09/900,241, filed on Jul. 6, 2001, now Pat. No. 7,105,017, said application No. 12/844,073 is a division of application No. 11/655,315, filed on Jan. 19, 2007, now abandoned, which is a division of application No. 10/299,882, filed on Nov. 19, 2002, now Pat. No. 7,175,651, which is a continuation-in-part of application No. 09/961,825, filed on Sep. 24, 2001, now abandoned, which is a continuation-in-part of application No. 09/900,241, filed on Jul. 6, 2001, now Pat. No. 7,105,017.

(60) Provisional application No. 60/283,108, filed on Apr. 11, 2001.

(51) Int. Cl.
*A61F 2/89* (2013.01)
*A61F 2/06* (2013.01)
*A61F 2/915* (2013.01)

(56) References Cited

U.S. PATENT DOCUMENTS

| | | | |
|---|---|---|---|
| 5,316,023 A | 5/1994 | Palmaz et al. |
| 5,578,072 A | 11/1996 | Barone et al. |
| 5,591,195 A | 1/1997 | Taheri et al. |
| 5,693,088 A | 12/1997 | Lazaraz |
| 5,728,131 A | 3/1998 | Frantzen et al. |
| 5,755,778 A | 5/1998 | Kleshinski |
| 5,769,887 A | 6/1998 | Brown et al. |
| 5,800,526 A | 9/1998 | Anderson et al. |
| 5,817,126 A | 10/1998 | Imran |
| 5,824,037 A | 10/1998 | Fogarty et al. |
| 5,824,040 A | 10/1998 | Cox et al. |
| 5,843,164 A | 12/1998 | Frantzen et al. |
| 5,925,061 A | 7/1999 | Ogi et al. |
| 5,928,281 A | 7/1999 | Huynh et al. |
| 5,944,750 A | 8/1999 | Tanner et al. |
| 5,968,091 A | 10/1999 | Pinchuk et al. |
| 5,997,573 A | 12/1999 | Quijano et al. |
| 6,015,422 A | 1/2000 | Kerr |
| 6,015,431 A | 1/2000 | Thornton et al. |
| 6,102,918 A | 8/2000 | Kerr |
| 6,102,940 A | 8/2000 | Robichone et al. |
| 6,110,198 A | 8/2000 | Fogarty et al. |
| 6,143,002 A | 11/2000 | Vietmeier |
| 6,152,956 A | 11/2000 | Pierce |
| 6,154,422 A | 11/2000 | Shinkawa et al. |
| 6,168,620 B1 | 1/2001 | Kerr |
| 6,206,661 B1 | 3/2001 | Iida et al. |
| 6,217,608 B1 | 4/2001 | Penn et al. |
| 6,224,626 B1 | 5/2001 | Steinke |
| 6,245,100 B1 | 6/2001 | Davila et al. |
| 6,273,909 B1 | 8/2001 | Kugler et al. |
| 6,290,666 B1 | 9/2001 | Devonec |
| 6,290,720 B1 | 9/2001 | Khosravi et al. |
| 6,319,278 B1 | 11/2001 | Quinn |
| 6,348,066 B1 | 2/2002 | Pinchuk et al. |
| 6,383,171 B1 | 5/2002 | Gifford et al. |
| 6,395,019 B2 | 5/2002 | Chobotov |
| 6,409,757 B1 | 6/2002 | Trout, III et al. |
| 6,464,719 B2 | 10/2002 | Jayaraman |
| 6,524,337 B1 | 2/2003 | Bergeron |
| 6,551,350 B1 | 4/2003 | Thornton et al. |
| 6,565,599 B1 | 5/2003 | Hong et al. |
| 6,602,280 B2 | 8/2003 | Chobotov |
| 6,652,580 B1 | 11/2003 | Chuter et al. |
| 6,695,875 B2 | 2/2004 | Stelter et al. |
| 6,712,843 B2 | 3/2004 | Elliott |
| 6,740,115 B2 | 5/2004 | Lombardi et al. |
| 6,749,628 B1 | 6/2004 | Callol et al. |
| 6,796,997 B1 | 9/2004 | Penn et al. |
| 6,858,037 B2 | 2/2005 | Penn et al. |
| 6,860,900 B2 | 3/2005 | Clerc et al. |
| 6,926,732 B2 | 8/2005 | Derus et al. |
| 6,929,709 B2 | 8/2005 | Smith |
| 7,147,660 B2 | 12/2006 | Chobotov et al. |
| 7,160,318 B2 | 1/2007 | Greenberg et al. |
| 7,175,652 B2 | 2/2007 | Cook et al. |
| 7,377,938 B2 | 5/2008 | Sarac et al. |
| 7,708,771 B2 | 5/2010 | Chuter et al. |
| 2003/0120338 A1 | 6/2003 | Chobotov et al. |
| 2003/0144725 A1 | 7/2003 | Lombardi |

FOREIGN PATENT DOCUMENTS

| | | |
|---|---|---|
| EP | 1 700 581 A2 | 9/2006 |
| FR | 2 765 097 | 12/1998 |
| SU | 1457921 | 2/1989 |
| WO | WO 9709007 A1 | 3/1997 |
| WO | WO-98/47447 | 10/1998 |
| WO | WO-99/39662 | 8/1999 |
| WO | WO-01/565501 | 8/2001 |

OTHER PUBLICATIONS

Cabinetmarking and Millwork—John L. Feirer.
The Complete Illustrated Guide to Joinery—Gary Rogowski, Section 1 Butt Joints—pp. 196-205.
Butt joint versus bevelled gold margin in metal-ceramic crowns—J.W. Mclean et al.
The American Heritage Dictionary of the English Language; Fourth Edition 2000.
ArtLex Art Dictionary.
GetWoodworking.com.
Vormann.com.
Wowimadeit.com.
Resch et al., The Impact of Stent Design on Proximal Stent-graft Fixation in the Abdominal Aorta: an Experimental Study, Eur J Vasc Endovasc Surg 20, 2000, pp. 190-195.

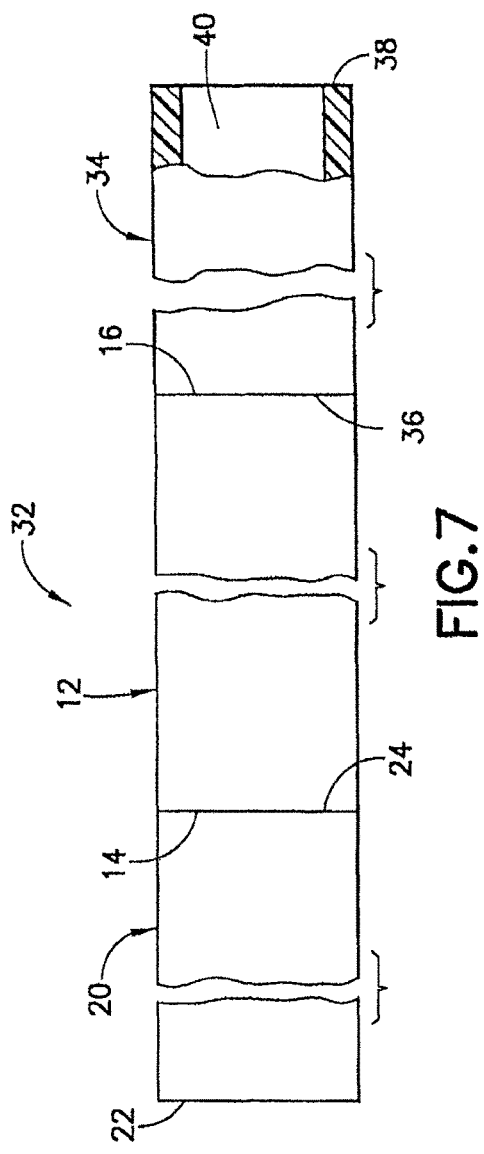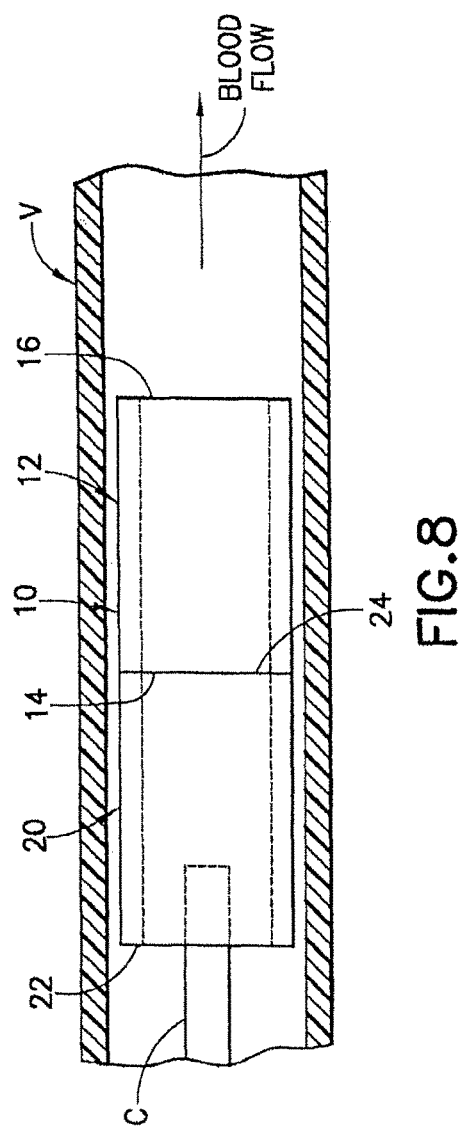

STENT/GRAFT ASSEMBLY

CROSS-REFERENCE TO RELATED APPLICATIONS

This application is a continuation of application Ser. No. 14/706,185 filed May 7, 2015 (pending), which is a continuation of application Ser. No. 13/933,522 filed Jul. 2, 2013 (now U.S. Pat. No. 9,050,182), which is a continuation of application Ser. No. 13/591,444 filed Aug. 22, 2012 (now abandoned), which is a continuation of application Ser. No. 12/844,073 filed Jul. 27, 2010 (now U.S. Pat. No. 8,257, 423), which is a divisional of application Ser. No. 12/137, 632 filed Jun. 12, 2008 (now abandoned), which is a divisional of application Ser. No. 10/849,652 filed May 20, 2004 (now abandoned), which is a continuation of application Ser. No. 09/900,241 filed Jul. 6, 2001 (now U.S. Pat. No. 7,105,017) and which in turn claims priority under 35 U.S.C. § 119(e) to U.S. provisional patent application 60/283,108 filed on Apr. 11, 2011. Application Ser. No. 12/844,073 also is a divisional of application Ser. No. 11/655,315 filed Jan. 19, 2007 (now abandoned), which is a divisional of application Ser. No. 10/299,882 filed Nov. 19, 2002 (now U.S. Pat. No. 7,175,651), which is a continuation-in-part of application Ser. No. 09/961,825, filed Sep. 24, 2001 (now abandoned) and a continuation-in-part of application Ser. No. 09/900,241 filed Jul. 6, 2001 (now U.S. Pat. No. 7,105,017) and said application Ser. No. 09/900,241 claims priority under 35 U.S.C. § 119(e) to U.S. provisional patent application 60/283,108 filed on Apr. 11, 2011, all of the foregoing are hereby incorporated by reference in their entirety herein.

BACKGROUND OF THE INVENTION

1. Field of the Invention

The subject invention relates to a stent and graft assembly for treating vascular anomalies, such as aneurysms.

2. Description of the Related Art

Vascular anomalies are considered to include blood vessels that are damaged, weakened or otherwise impaired. The anomaly may include a local change in the cross-sectional dimensions of the blood vessel. For example, aneurysms include a local area where a blood vessel expands to a larger cross-sectional area due to disease, weakening or other damage.

The aorta extends from the heart and through the abdomen. The abdominal aorta then feeds abdominal organs and the right and left iliac arteries that bring blood to the right and left legs respectively. The aorta is prone to aneurysms. Aortic aneurysms that are not treated in a timely manner can lead to rupture, occlusion, infection or the production of emboli which can flow downstream and occlude a smaller blood vessel. A ruptured aortic aneurysm typically is fatal due to a loss of the large volume of blood that flows through the abdominal aorta.

Aneurysms can be corrected by grafts. The typical graft is implanted surgically by accessing the site of the aneurysm, cutting open the aneurysm and then surgically forming an appropriate fabric into a tubular shape that spans the aneurysm. Thus, upstream and downstream ends of the prior art graft are sutured to healthier regions of the blood vessel.

The prior art also includes endovascular grafts. An endovascular graft comprises a flexible tubular member formed from a synthetic fabric. The graft is selected to have an outside cross-sectional dimension that approximates the inside cross-sectional dimensions of the blood vessel on either side of the aneurysm. The graft also is selected to have a length that exceeds the length of the damaged area of the blood vessel.

An unsupported flexible tubular graft has a tendency to collapse in the presence of the flowing blood and could be transported downstream by the blood flow. As a result, endovascular grafts are used in combination with a stent. Stents take many forms, including balloon expandable stents and self-expanding stents, but typically are resilient cylindrical members that are inserted axially through the tubular graft prior to insertion into the blood vessel. The stent and the graft are sutured together prior to deployment so that the opposed ends of the stent align with the opposed ends of the graft. The endovascular graft assembly then is inserted through a healthy region of the blood vessel and is advanced through the circulatory system to the aneurysm or other damaged region of the blood vessel. More particularly, the endovascular graft assembly is advanced to a position where the endovascular graft assembly bridges the aneurysm or other damaged portion of the blood vessel. However, the opposed axial ends of the endovascular graft assembly extend beyond the aneurysm. The stent then is expanded to hold the graft in an expanded tubular condition with at least the opposed axial end regions of the graft being urged tightly against the interior of healthy regions of the blood vessel. The stent and the graft of the prior art endovascular graft assembly are coaxial, and longitudinally coextensive.

Prior art assemblies of stents and grafts typically perform well. However, the coaxially and longitudinally coextensive arrangement of the stent and graft has resulted in a cross-sectionally large assembly. A cross-sectionally large graft and stent assembly can be difficult to insert and deliver intravascularly to the damaged section of the blood vessel and may require surgery.

The inventor herein has developed low-profile stent/graft structures, as shown for example in U.S. Pat. No. 6,015,422, U.S. Pat. No. 6,102,918 and U.S. Pat. No. 6,168,620.

In view of the above, it is an object of the subject invention to provide improvements in vascular stent and graft assemblies that provide a small cross-section and low profile.

It is also an object of the invention to provide an endovascular stent and graft assembly that can be introduced easily into and through the damaged or diseased section of a blood vessel.

A further object of the subject invention is to provide a system of endovascular stents and grafts that can be assembled intravascularly through damaged regions of a blood vessel.

SUMMARY OF THE INVENTION

The subject invention is directed to an endovascular graft assembly that comprises at least one tubular vascular graft and at least one fixation device. The tubular graft and the fixation device are connected substantially in end-to-end relationship with little or no longitudinal overlap. In certain embodiments, the substantially end-to-end relationship of the tubular graft and the fixation device may include a small axial space between the tubular graft and the fixation device. One or more connecting wires may bridge the space between the axially align tubular graft and fixation device. The tubular graft has a length that exceeds the length of a damaged section of a blood vessel that is being repaired by the endovascular graft assembly. The tubular graft also has a cross-sectional size that is about 10%-30% wider than the cross-sectional size of the blood vessel that is being repaired.

The tubular graft preferably is formed from a synthetic material, such as a material formed from an ultra thin polyester fiber, or other vascular graft materials known to those skilled in this art.

The fixation device may comprise a generally tubular stent. One end of the tubular stent is securely affixed to one end of the tubular graft. The end-to-end fixation of the graft to the stent preferably is carried out with little or no telescoping between the tubular graft and the stent. However, a slight amount of telescoping (e.g. 0-20 mm) may be required to ensure a secure and substantially permanent interengagement. The connection between the tubular graft and the tubular stent may be achieved by hooking, stitching, fusing or other such secure connection techniques. The connection need not be continuous around the peripheries of the stent and the tubular graft. Thus, the stent and the tubular graft merely may be connected at one location on their respective ends or at plural spaced-apart locations.

The fixation device need not be a tubular stent. Rather, the fixation device may comprise a plurality of hooks that extend from at least one longitudinal end of the tubular graft. The hooks can be engaged with healthy sections of blood vessel on either side of an aneurysm. The fixation device may further include an annular ring affixed to an axial end of the tubular graft, and the hooks may project axially from the ring. The ring functions to keep the tubular graft open during insertion of the endovascular graft assembly into the blood vessel.

The endovascular graft assembly further comprises an internal stent to provide radial support for the tubular graft of the endovascular graft assembly. However, unlike prior art endovascular graft assemblies, the internal stent of the subject invention is deployed after the end-to-end assembly of the fixation device and tubular graft have been positioned properly across the aneurysm. The internal stent may be a balloon expandable stent or a self-expanding stent. However, the insertion of the internal stent after the insertion of the end-to-end assembly of the fixation device and tubular graft greatly facilitates the deployment of the entire endovascular stent/graft assembly to the proper location.

The endovascular graft assembly may further include at least one support that extends from the fixation device into the graft to prevent the graft from collapsing radially or axially during or after installation and/or to provide radially outward support for the graft. The support may comprise at least one longitudinally extending wire extending from the fixation device substantially entirely through the graft and then anchored at the axial end of the graft opposite the stent. The support may alternatively comprise a coil extending substantially from the fixation device, through the graft and to the end of the graft opposite the fixation device. The support may be connected to the fixation device or unitary with portions of the fixation device.

The endovascular graft assembly may comprise at least two fixation devices connected respectively to opposite ends of a tubular graft. The endovascular graft assembly may further comprise a plurality of tubular grafts connected respectively to opposite axial ends of fixation devices. The tubular graft and tubular fixation devices need not be all of identical cross-sectional sizes. Additionally, the assembly may comprise plural fixation devices connected axially to the legs or branches of a bifurcated or trifurcated graft, such as a graft having an inverted Y-shape. Furthermore, certain components of the assembly may be assembled intravascularly and intraoperatively. The end-to-end connection of a tubular fixation device and a tubular graft provides advantages over a graft that is at least partly coextensive with a tubular stent. In particular, the cross-sectional dimension of the preferred assembly is smaller than an assembly with the tubular graft and tubular stent at least partly coextensive with one another, and hence insertion is easier. However, the end-to-end axial connection of a tubular graft with a tubular fixation device has advantages that can be applied to a coextensive tubular graft and tubular stent. For example, one or more tubular grafts may be assembled preoperatively with one or more tubular stent. This assembly can include a single tubular graft with a single tubular stent inwardly therefrom, a tubular graft with a plurality of axially spaced tubular stents inwardly therefrom or an assembly with one or more tubular stents disposed between concentrically disposed inner and outer tubular grafts. Any of these tubular stent/graft assemblies can be connected in end-to-end relationship with a fixation device. Such an end-to-end combination would not achieve the small cross-section and easy insertion of the above reference preferred embodiment. However, the end-to-end connection of a fixation device and an assembly with a tubular graft and one or more tubular stents can achieve enhanced fixation and can prevent the assembly of the tubular graft and tubular stents from drifting in the blood vessel.

The tubular graft and the fixation device includes connected ends that are connected to one another in substantially end-to-end relationship and free ends that are not connected to one another. Thus, the free end of the tubular graft is at the end of the endovascular graft assembly remote from the fixation device. Similarly, the free end of the fixation device is at the end of the endovascular graft assembly remote from the tubular graft.

The endovascular graft assembly may be deployed with an introducer sheath or other such deployment device. The introducer sheath or other such device is an elongate member that may be substantially tubular and has a cross sectional area less than the cross sectional area of the blood vessel that requires repair. The introducer sheath or other such introducing device has a leading end and an opposed trailing end that may be a hub. The free end of the tubular graft is attached releasably to the leading end of the introducer sheath or other such deployment device. Additionally, the free end of the fixation device of the endovascular graft assembly is farther from the leading end of the introducer sheath or other such deployment device, and hence nearer to the trailing end the introducer sheath.

The endovascular graft assembly may be introduced into a blood vessel that requires repair. This introduction is carried out so that the free end of the tubular graft leads the fixation device into the blood vessel. The tubular graft is moved through the blood vessel and slightly beyond the region of the blood vessel that requires repair. The fixation device then is moved axially within the tubular graft and towards the leading end of introducer sheath or other such deployment device. This movement of the fixation device is carried out independently of the tubular graft and hence causes the tubular graft to be turned substantially inside out. More particularly, the connected end of the tubular graft begins moving axially within the tubular graft and toward the free end of the tubular graft. Sufficient movement will cause the connected end of the tubular graft to advance axially beyond the free end of the tubular graft. The relative positions of the free end of the tubular graft and the free end of the fixation device will depend upon the exact characteristic of the aneurysm or other such vascular anomaly that is being corrected. In some instances, the connected ends of the tubular graft and the fixation device will be aligned with one another and both will be axially beyond the free end of the tubular graft. In other instances, the connected end of the fixation device will move axially beyond both ends of the tubular graft. In this situation, the substantially end-to-end connection of the tubular graft and the fixation device will define a connector with a slight axial gap. In some instances, the free end of the fixation device will be within the tubular graft. In other instances, the free ends of the fixation device will project axially beyond the free end of the tubular graft.

All of these embodiments simplify deployment of the endovascular graft assembly. In this regard, the endovascular graft assembly achieves the small cross sectional dimension due to the end-to-end connection of the tubular graft and the fixation device during deployment. However, unlike prior art endovascular graft assemblies, there is generally no need for an additional deployment of an internal stent to hold the tubular graft in an expanded position. Rather, the stent of the endovascular graft assembly performs the function of the internal stent. Sutures or other connectors known to those skilled in the art may connect the free end of the tubular graft to the leading end of the introducer sheath or other such deployment device. The sutures, however, may form a connection that is easily releasable. The endovascular graft assembly may include means for inverting the tubular graft or turning the tubular graft inside.

The tubular graft may be a bifurcated graft with a single tubular connected end joined to the connected end of the fixation device in substantially end-to-end relationship. The bifurcated graft may further include first and second tubular legs of the bifurcated graft with first and second free ends. This embodiment of the endovascular graft assembly may be deployed substantially in the manner described above. In particular, one leg of the tubular graft may be inverted and passed interiorly into the opposed leg. This embodiment may be deployed substantially in the manner of the previous embodiment. However, after a final stage of deployment, the stent or other such fixation device will be moved axially within the bifurcated graft to a point beyond the bifurcation. The inverted leg will then be reoriented so that the bifurcated graft assumes a generally Y-shaped configuration. As before, the endovascular graft assembly in accordance with this embodiment provides for low profile deployment and permits the assembly to be used without an additional internal stent.

BRIEF DESCRIPTION OF THE DRAWINGS

FIG. 7 is an elevational view of an endovascular stent/graft assembly in accordance with a second embodiment of the invention.

FIG. 8 is a schematic illustration of the endovascular stent/graft assembly of FIG. 1 inserted into a blood vessel.

DETAILED DESCRIPTION OF THE PREFERRED EMBODIMENTS

Figure 1:
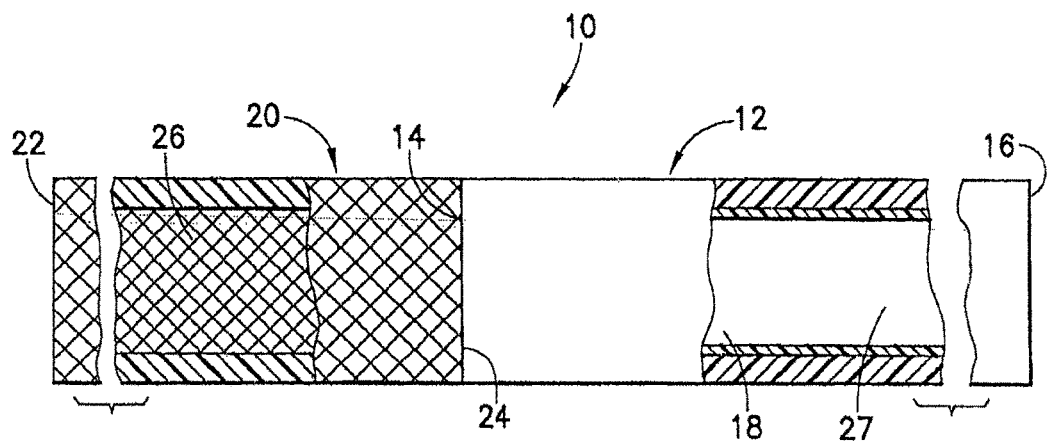
FIG. 1 is an elevational, partly in section, view of an endovascular stent/graft assembly in accordance with a first embodiment of the invention.

An endovascular stent/graft assembly in accordance with a first embodiment of the invention is identified generally by the numeral 10 in FIG. 1. The endovascular stent/graft assembly 10 includes a substantially tubular graft 12 having a flexible wall formed from a synthetic material, such as a polyester material that is substantially impervious to fluid transmission or that becomes substantially impervious after exposure to blood. The tubular graft 12 has an upstream end 14, a downstream end 16 and a fluid passage 18 extending between the ends. The endovascular stent/graft assembly 10 further comprises a tubular stent 20 having an upstream end 22, a downstream end 24 and a passage 26 extending between the ends. The tubular stent 20 may be of known construction and may be formed from materials that are known to those skilled in the art of treating vascular anomalies with endovascular stent/graft assemblies, such as polyethylene terepthalate and PTFE, including materials sold under the trademarks DACRON® and GORTEX®.

The terms upstream and downstream used to define the ends of the tubular graft 12 and the tubular stent 20 are employed with reference to the direction of blood flow existing during insertion of a stent graft assembly 10. More particularly, the endovascular stent/graft assembly preferably will be inserted into a blood vessel such that the tubular stent 20 is upstream and facing into the flow of blood. The tubular graft 12 then will trail behind the stent relative to the direction of insertion of the endovascular stents/graft assembly 10 and relative to the direction of the blood flow. This preferred orientation of the endovascular stent/graft assembly 10 will enable the much more flexible tubular graft 12 to perform much in the nature of a wind-sock that is urged into an extended condition by forces exerted by the blood flow. A reversed insertion, of this first embodiment, on the other hand, could cause the flexible tubular graft 12 to collapse in response to the blood flow.

Figure 2:
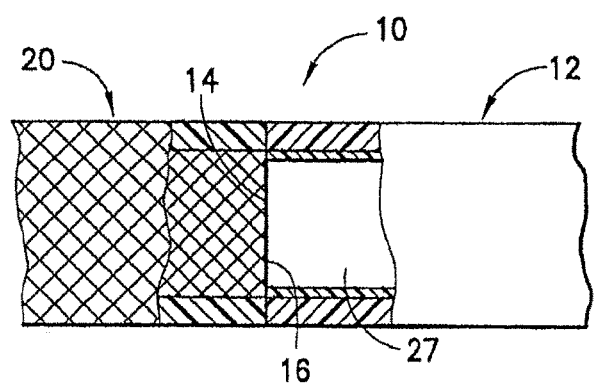
FIG. 2 is an enlarged elevational view, partly in section, of a connection between the stent and graft of the assembly in either FIG. 1.
Figure 3:
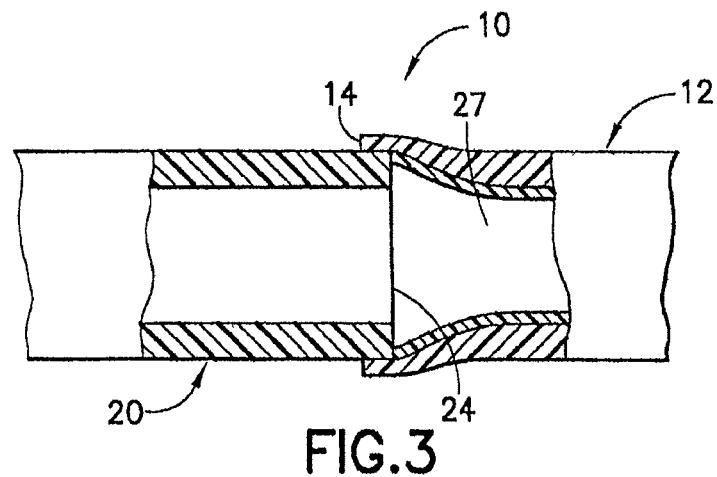
FIG. 3 is an enlarged elevational view partly in section, similar to FIG. 2, but showing an alternate connection between the stent and the graft.

As shown generally in FIG. 1 and more specifically in FIGS. 2 and 3, the tubular graft 12 and the tubular stent 20 are connected substantially in end-to-end axial relationship. More particularly, as shown in FIG. 2, the upstream end 14 of the tubular graft 12 is butted against the downstream end 24 of the tubular stent 20 to achieve a true end-to-end axial connection between the tubular graft 12 and the tubular stent 20. This pure axial end-to-end abutment can be achieved by fusing, suturing or other known connection means that will be appreciated by persons skilled in this art.

The true end-to-end axial connection may be difficult to achieve with certain material employed for the tubular graft and the tubular stent. In these situations, a substantially end-to-end axial connection can be achieved with a slight telescoping overlap as shown schematically in FIG. 3. With this optional arrangement, the inner circumferential surface of the tubular graft 12 adjacent the upstream end 14 may be telescoped slightly over the outer circumferential surface of the tubular stent 20 adjacent the downstream end 24. Sutures, fusing or other known connections then may be employed to permanently affix the slightly overlapped ends of the tubular graft 12 and the tubular stent 20.

FIGS. 2 and 3 depict substantially continuous connection between the annular periphery at the upstream end of the tubular graft 12 and the annular periphery at the downstream end 24 of the tubular stent 20. However, such a continuous connection may not be required in many situations. Rather, one or more points of contact and affixation may be sufficient between the upstream end 14 of the tubular graft 12 and the downstream end of the tubular stent 20. As noted above, end-to-end axial connection may comprise true end-to-end connection or a connection with a slide telescope overlap between the tubular graft 12 and the tubular stent 20, as shown in FIG. 3.

Figure 4A:
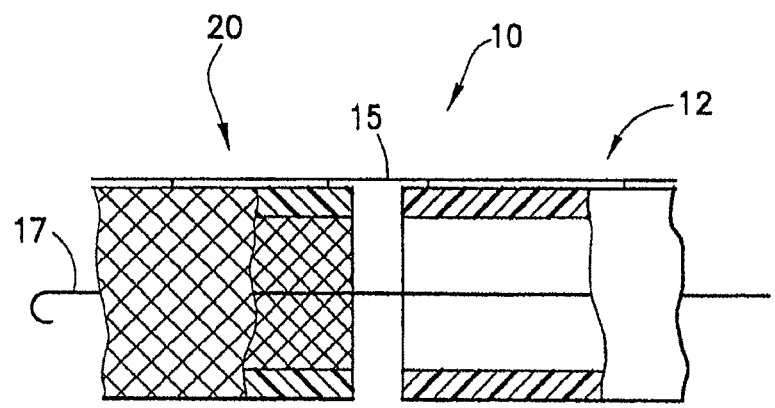
FIGS. 4A and 4B are enlarged elevational views, partly in section, showing a further alternate connection between the stent and the graft.
Figure 4B:
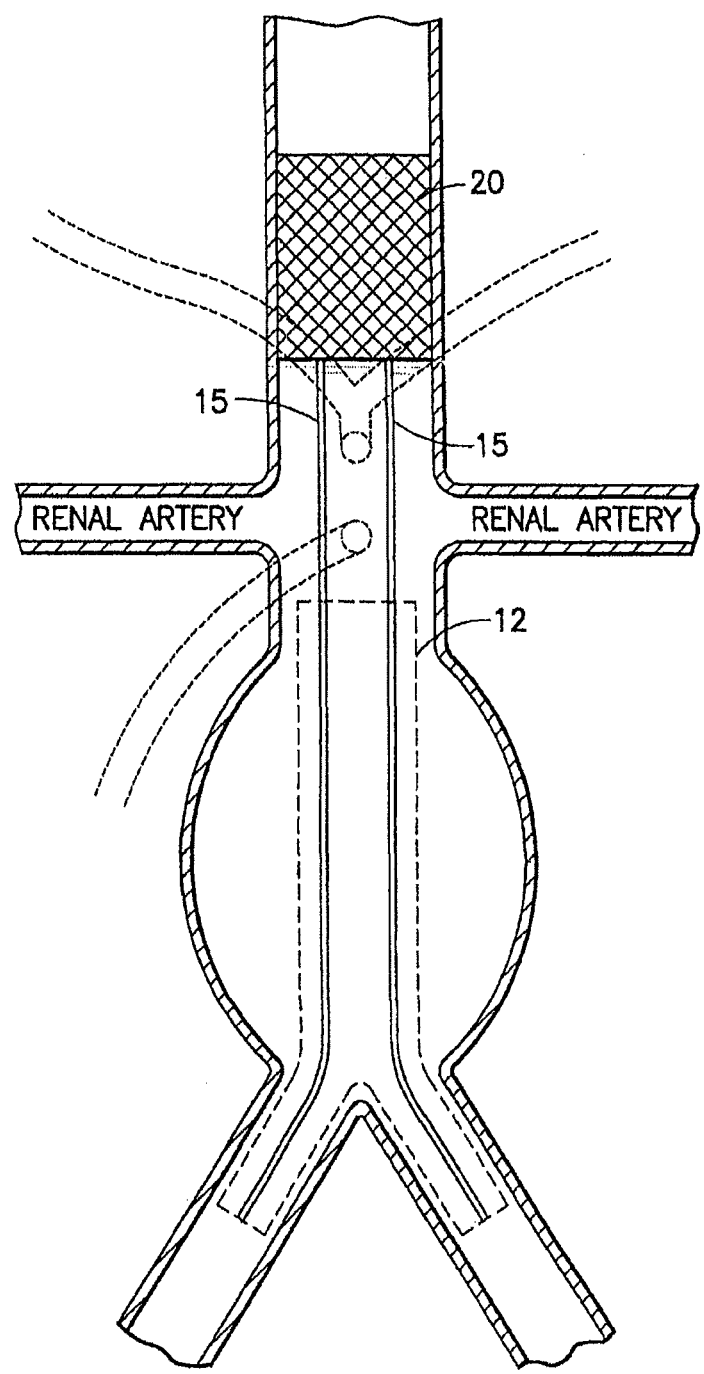

As a further alternate, substantially end-to-end axial relationship may comprise an axial gap between the tubular graft 12 and the tubular stent 20, as shown in FIGS. 4A and 4B. FIG. 4A shows the general concept of an axial gap between the tubular graft 12 and the tubular stent 20 prior to deployment. FIG. 4B shows one optional deployment. The axial spacing can provide even further advantages for the deployment and positioning of the tubular graft 12 and the tubular stent 20. In this embodiment, at least one connecting wire 15 is connected to both the tubular graft 12 and the tubular stent 20 and bridges the gap between the axially aligned tubular graft 12 and tubular stent 20. The connecting wire 15 maintains the spaced disposition between the tubular graft 12 and the tubular stent 20. In this embodiment, as well as others, a guide wire 17 may be used to guide the stent/graft assembly 10 during deployment. With reference to FIG. 4B, the tubular stent 20 may be disposed upstream from the renal arteries and upstream from the visceral arteries shown by broken lines in FIG. 4. The tubular graft 12 has an upstream end disposed between the aneurysm and the renal arteries. The wires 15 extend between the graft 12 and the tubular stent 20. Hence, the stent/graft assembly is anchored efficiently in a healthy section of the aorta upstream from the aneurysm. Additionally, blood flow to and from the renal arteries and the visceral arteries is ensured by the axial gap between the tubular graft 12 and the stent 20. The wires 15 bridge the gap between the graft 12 and the stent 20.

The endovascular stent/graft assembly 12 further comprises an internal stent 27 that is deployed after the end-to-end connected tubular graft 12 and tubular stent 20 are in place. The internal stent 27 may be a balloon expandable stent or a self-expanding stent and functions to maintain tubular graft 12 in an expanded non-occluded condition. Furthermore, the internal stent 27 maintains outer circumferential surface regions of the tubular graft 12 near the upstream and downstream ends 14 and 16 in face-to-face engagement with the inner surface of the blood vessel upstream and downstream from the aneurysm. The insertion of the internal stent 27 after positioning the tubular graft 12 and the tubular stent 20 is considerably easier than the prior art endovascular grafts that simultaneously attempt to advance a coaxial arrangement of graft and stent that are longitudinally coextensive with one another.

Figure 5:
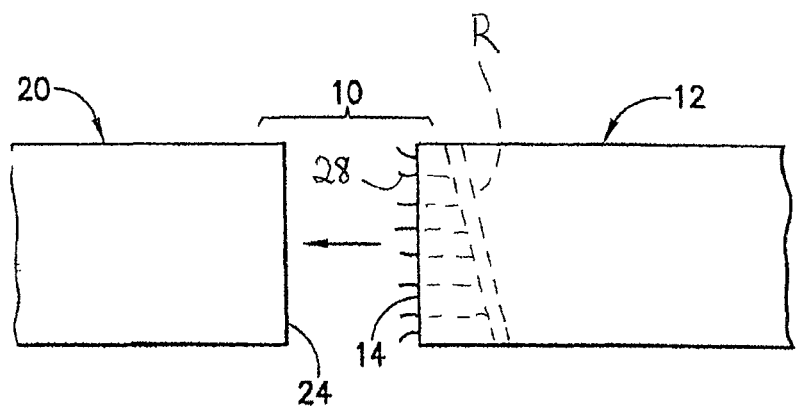
FIG. 5 is an elevational view of the graft with hooks for fixation to the stent or to a blood vessel.
Figure 6:
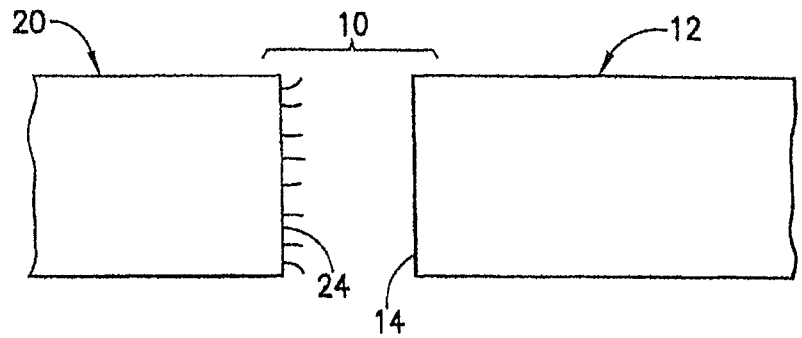
FIG. 6 is an elevational view similar to FIG. 5, but showing hooks on the tubular stent.

An alternate end-to-end connection between the tubular graft 12, as shown in FIG. 5, includes a plurality of hooks 28 woven or otherwise incorporated into the tubular graft 12 to extend axially beyond at least the upstream end 14. The hooks 28 on the upstream end 14 of the tubular graft 12 can be engaged into the circumferential surface of the blood vessel. Thus, the hooks 28 function as a fixation device that is an alternate to the tubular stent 20 shown in FIGS. 1-3. The hooks 28 can be mounted to an annular ring (not shown) that can be affixed to the upstream end 14 of the tubular graft 12. Thus, the combination of the ring and the hooks 28 may function as the fixation device. A variation of the FIG. 5 embodiment, the hooks 28 at the upstream end 14 of the tubular graft 12 can be engaged into portions of the tubular stent 20 adjacent the downstream end 24. Alternatively, as shown in FIG. 6, hooks 30 may extend axially beyond the downstream end 24 of the tubular stent 20 for engagement with portions of the tubular graft 12 adjacent the upstream end 14.

FIG. 7 shows an endovascular stent/graft assembly 32 in accordance with a second embodiment of the invention. The endovascular stent/graft assembly 32 includes a tubular graft 12 substantially identical to the tubular graft 12 in the embodiment of FIG. 1. The stent/graft assembly 32 further includes an upstream tubular stent 20 substantially identical to the tubular stent 20 in the embodiment of FIG. 1. However, the stent/graft assembly 32 further includes a downstream stent 34. The downstream stent 34 has an upstream end 36, a downstream end 38 and a tubular passage 40 extending between the ends. The upstream end 36 of the downstream stent 34 is connected in substantially end-to-end relationship with the downstream end 16 of the tubular graft 12 by any of the connection arrangements depicted respectively in FIGS. 2-6. The downstream stent 34 can be connected to the tubular graft prior to insertion of the stent/graft assembly 32 into the blood vessel. Alternatively, the sub-assembly of the tubular graft 12 and the upstream stent 20 can be inserted into the blood vessel substantially as shown in FIG. 1. The downstream stent 34 then can be inserted subsequently and connected intraoperatively to the downstream end 16 of the tubular graft 12.

Figure 9:
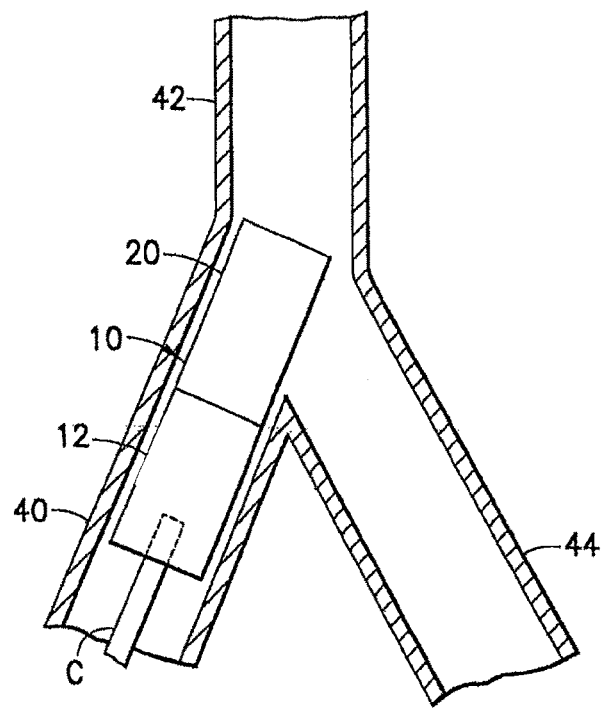
FIG. 9 is a schematic illustration of an insertion of the endovascular stent/graft assembly of FIG. 1 into the abdominal aorta.

As noted above, and as illustrated generally in FIG. 1, the endovascular stent/graft assembly 10 is fixed into the blood vessel with the tubular graft 12 in a downstream position relative to the tubular stent 20. This orientation, does not, however, imply a required direction of insertion. For example, as depicted in FIG. 8, a catheter C is employed to insert the endovascular stent/graft assembly 10 into a blood vessel V along the direction of flow and the tubular graft 12 leading the tubular stent 20. Thus, despite the slow movement of the catheter C and the stent/graft assembly 10 through the blood vessel V in the direction of the blood flow, the tubular graft 12 will extend axially beyond the tubular stent 20 with a substantially wind-sock effect as described above and as shown in FIG. 8. Alternatively, the catheter C can be used to insert the endovascular stent/graft assembly 10 in opposition to the direction of blood flow, but with the tubular stent 20 in the upstream position and leading the endovascular stent/graft assembly 10 into the direction of blood flow. More specifically, FIG. 9 schematically depicts the insertion of the endovascular stent/graft assembly 10 through the right iliac artery 40 and into the abdominal aorta 42, with the tubular stent 20 in the upstream position relative to the tubular graft 12, and with the tubular stent 20 leading the insertion against the direction of blood flow.

Figure 10:
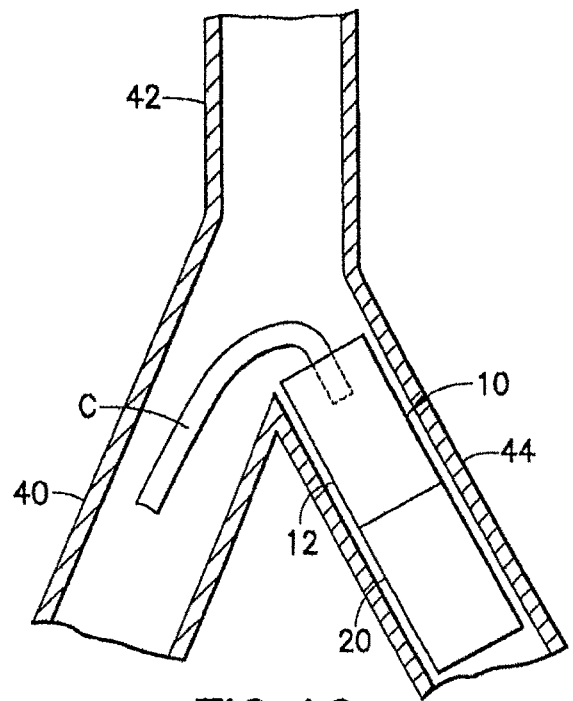
FIG. 10 is a schematic illustration of the endovascular stent/graft assembly of FIG. 1 deployed through the right iliac artery and then inserted into the left iliac artery.

In certain procedures, the stent/graft assembly may start in a direction against the flow of blood but move into a different blood vessel to follow the flow of blood. More particularly, FIG. 10 depicts the insertion of the stent/graft assembly 10 into the right iliac artery 40 for eventual insertion into the left iliac artery 44. The initial part of this insertion will have the endovascular stent/graft assembly 10 inverted relative to the preferred and eventual orientation. Thus, the tubular graft 12 may initially be in an upstream position, and accordingly may collapse somewhat during the initial stages of the insertion. However, the tubular graft 12 of the stent/graft assembly will move into the downstream position relative to the tubular stent 20 as the stent/graft assembly 10 moves into the left iliac artery 44. Thus, any collapsing of the more flexible graft 12 that may have occurred during initial insertion through the right iliac artery 40 will be offset by the above-described wind-sock effect as the stent/graft assembly 10 moves into the left iliac artery 44.

Figure 11:
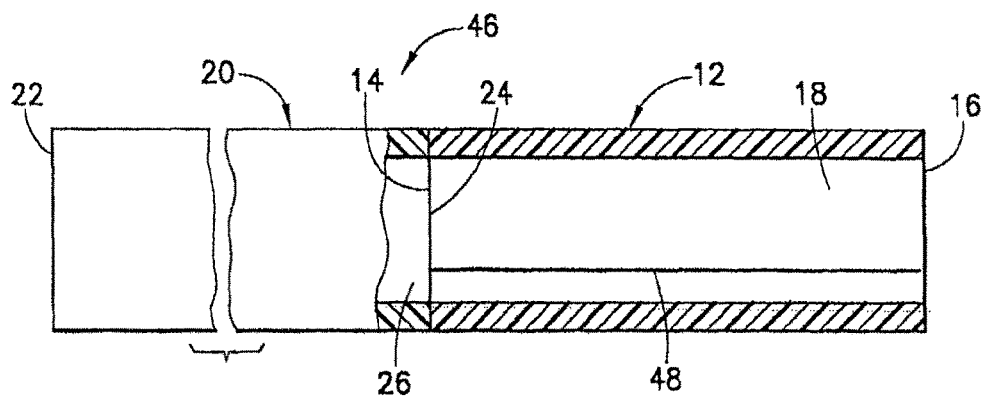
FIG. 11 is an elevational view, partly in section of a third alternate endovascular stent/graft assembly.

In certain instances, it may be desirable to provide support for the tubular graft 12 of the stent/graft assembly 10. For example, a third embodiment of the endovascular stent/graft assembly is identified generally by the numeral 46 in FIG. 11. The endovascular stent/graft assembly 46 includes a tubular graft 12 with an upstream end 14, a downstream end 16 and a tubular passage therebetween, substantially as in the first and second embodiments. The stent/graft assembly 46 further includes a tubular stent 20 having an upstream end 22, a downstream end 24 and a tubular passage 26 extending between the ends. As in the first embodiment, the upstream end 14 of the tubular graft 12 is affixed in substantially end-to-end relationship with the downstream end 24 of the tubular stent 20. The endovascular stent/graft assembly 46 differs from the first embodiment by the inclusion of a single wire 48 extending from the tubular stent 20 axially along the tubular graft 12 and affixed to the tubular graft 12 in proximity to downstream end 16. The wire 48 ensures that the tubular graft 12 will remain substantially in an extended condition and will prevent the downstream end 16 of the tubular graft 12 from collapsing toward the tubular stent 20. The provision of the wire 48 may be helpful, for example, in instances depicted in FIG. 10 where an endovascular stent/graft assembly may travel in counter flow direction with the tubular graft 12 in an upstream position relative to the tubular stent 20. Thus, the wire 48 allows the assembly 46 to be deployed with the tubular stent 20 downstream of the tubular graft 12 when there is no upstream landing place for the tubular stent 20. A second internal stent, such as the internal stent 27 of FIG. 1, then is deployed to open the tubular graft 12. In this embodiment, the wind sock effect does not occur.

Figure 12:
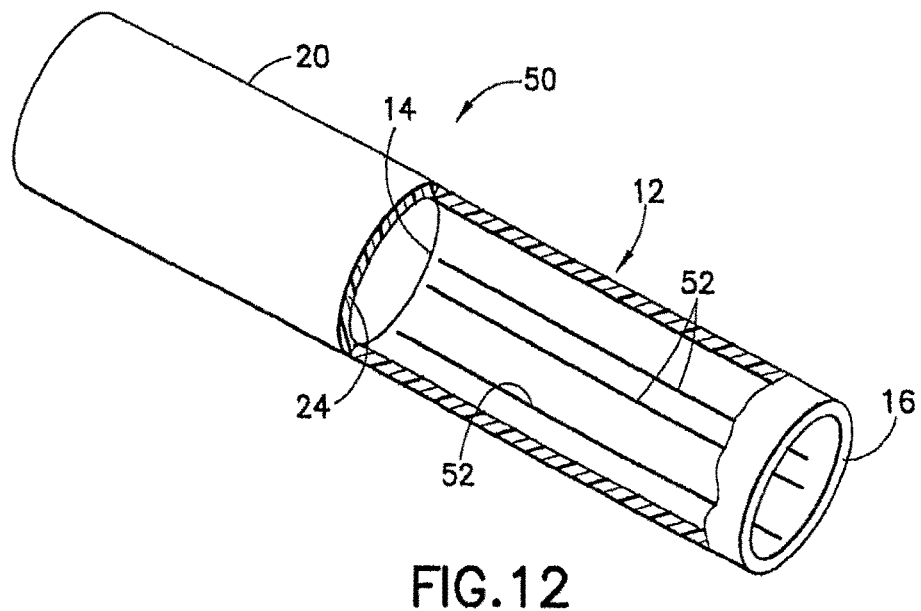
FIG. 12 is a perspective view of a fourth embodiment of an endovascular stent/graft assembly in accordance with the subject invention.

A fourth embodiment of the endovascular stent/graft assembly is identified by the numeral 50 in FIG. 12. The endovascular stent/graft assembly 50 is a variation of the stent/graft assembly 46 of FIG. 11 in that a plurality of wires 52 extend axially from the stent 20 substantially to the downstream end 16 of the tubular graft 12 where the wires 52 are affixed to the tubular graft 12. The stent/graft assembly 50 prevents axial collapsing of the tubular stent 20, substantially as with the embodiment of FIG. 11. However, the wires 52 will further provide radially support for the tubular graft 12 and will resist radially collapsing of the graft 12.

Figure 13:
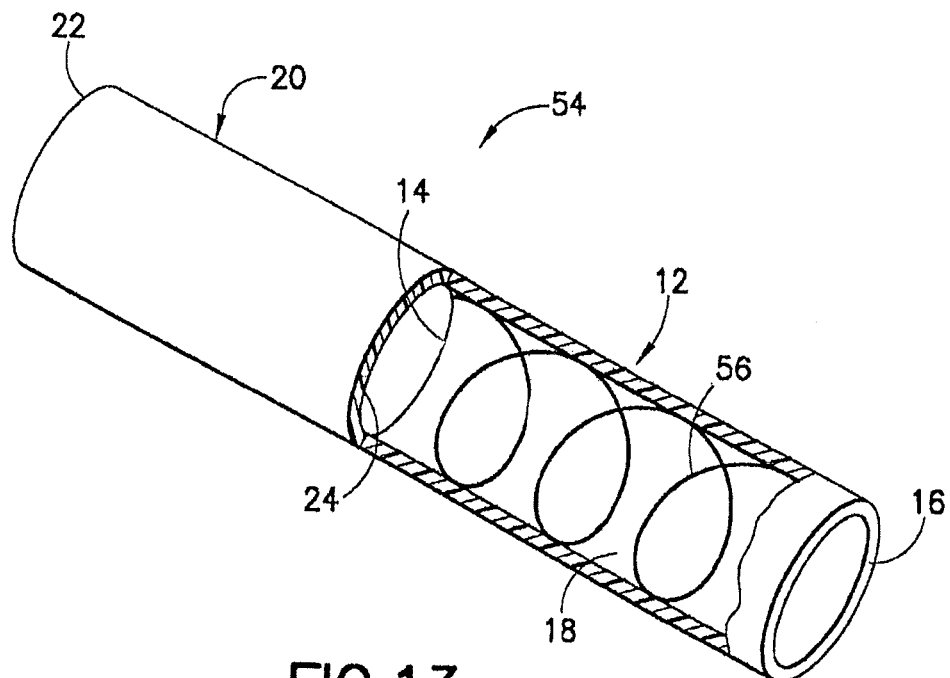
FIG. 13 is a perspective view of an endovascular stent/graft assembly in accordance with a fifth embodiment of the subject invention.
Figure 14:
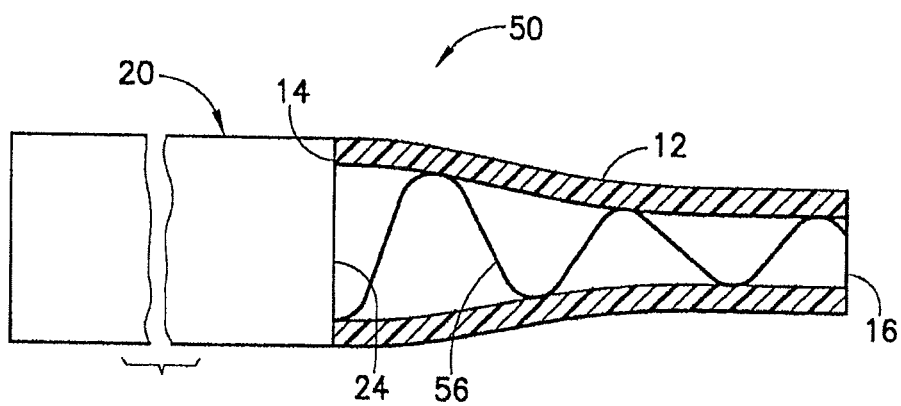
FIG. 14 is a side elevational view of the endovascular stent/graft assembly of FIG. 13 with a cross-sectional variation along the length of the graft to accommodate cross-sectional variations of the blood vessel.

A fifth embodiment of the endovascular stent/graft assembly is identified by the numeral 54 in FIGS. 13 and 14. The stent/graft assembly 54 is similar to the stent/graft assemblies of FIGS. 11 and 12. However, the axially aligned wires of the previous embodiment are replaced with a coil 56. The coil 56 may be anchored to the tubular stent 20 or to the upstream end 14 of the tubular graft 12 for affixation to the downstream end 16 of the tubular graft 12. The coil 56 resists axially collapsing and will assist with axial extension in response to any axial collapse that does occur. Additionally, the coil 56 provides greater outwardly directed radially forces on the tubular graft 12 then either of the previous embodiments.

Figure 15:
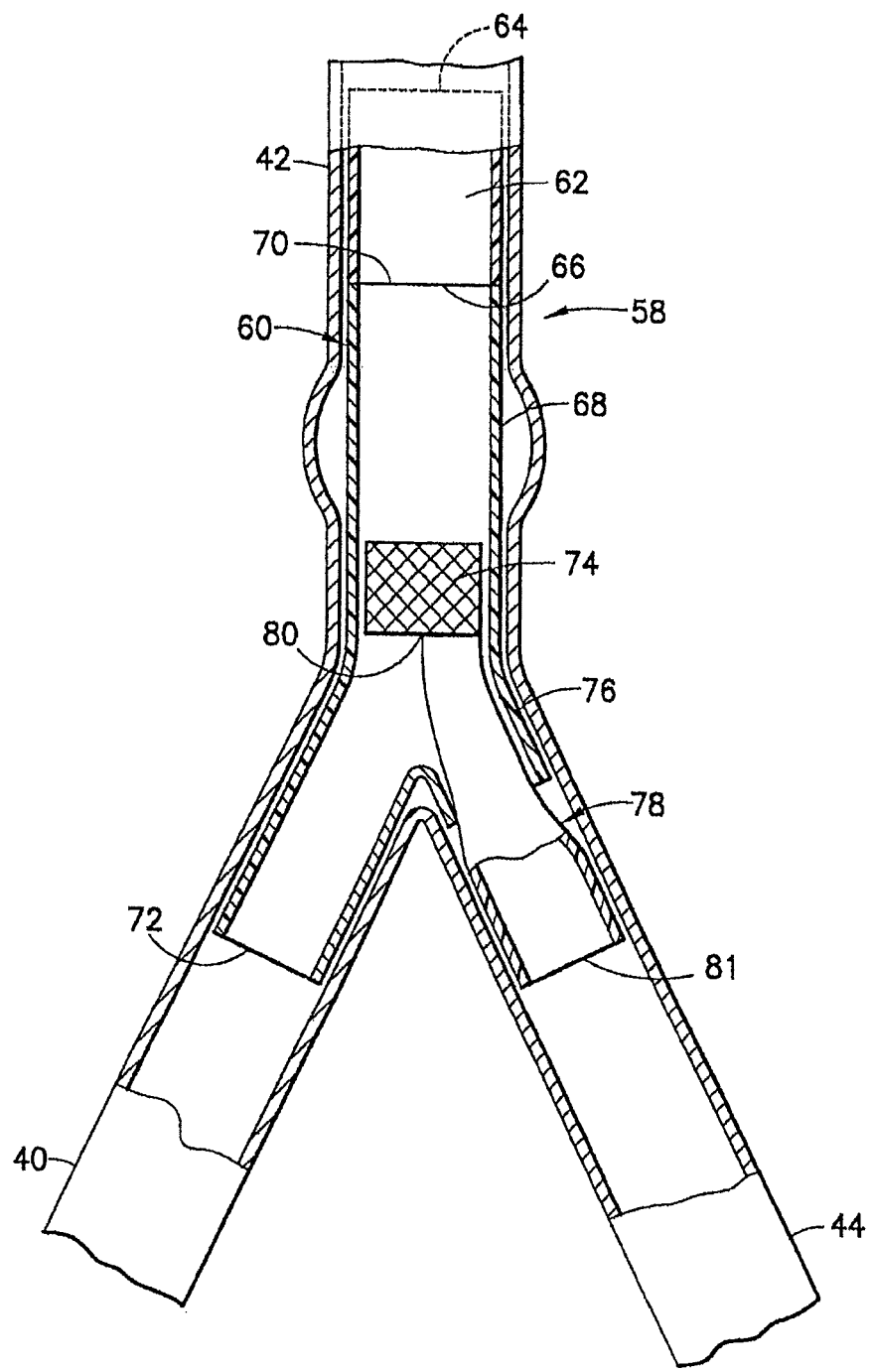
FIG. 15 is a schematic view of a modular endovascular stent/graft assembly that represents a sixth embodiment of the invention intended primarily for deployment into the abdominal aorta and adjacent regions of the left and right iliac arteries.

The endovascular stent/graft assembly 32 of FIG. 7 shows that a plurality of stents 20, 34 can be assembled with a single tubular graft 12. The principles embodied in FIG. 7 can be employed further to develop more complex modular assemblies. For example, FIG. 15 shows a modular assembly for repairing vascular anomalies in the region where the abdominal aorta 42 meets the right iliac artery 40 and the left iliac artery 44. In particular, the modular endovascular stent/graft assembly 58 comprises a first modular subassembly 60 with a first tubular stent 62 with an upstream end 64 and an opposed downstream end 66. The first modular subassembly 60 further comprises a first tubular graft 68 with an upstream end 70 connected substantially in end-to-end axial relationship with the downstream end 66 of the first stent 62. The first tubular graft 68 further includes a downstream end 72. The first modular component 60 is deployed from a right leg approach into the right iliac artery 40. The first tubular stent 62 then is advanced sufficiently into the abdominal aorta 42 for the first tubular stent 62 to be upstream of the aneurysm or other vascular abnormality in the abdominal aorta 42.

The modular assembly 60 further includes a second tubular stent 74 that is mounted unrestrained in the first tubular graft 68 at a location downstream from or within the aneurysm. The first tubular graft 68 further includes tubular exit 76 at a location between the second tubular stent 74 and the downstream end 72 of the first tubular graft. The second tubular stent 74 preferably is cross-sectionally larger than both the exit 76 and portions of the first tubular graft 68 in proximity to the exit 70. Thus, the unrestrained second tubular stent 74 will not slip longitudinally into either the exit 76 or downstream portions of the first tubular graft 68.

The assembly 58 further includes a second tubular graft 78 with an upstream end 80 and a downstream end 81. The second tubular graft 78 is deployed from a left leg approach into the left iliac artery 44 and is advanced through the exit 76 of the first tubular graft 68. The upstream end 80 of the second tubular graft 78 is connected substantially end-to-end with the second tubular stent 74. Internal stents then may be inserted, such as the internal stent 27 described with respect to the first embodiment.

Figure 16:
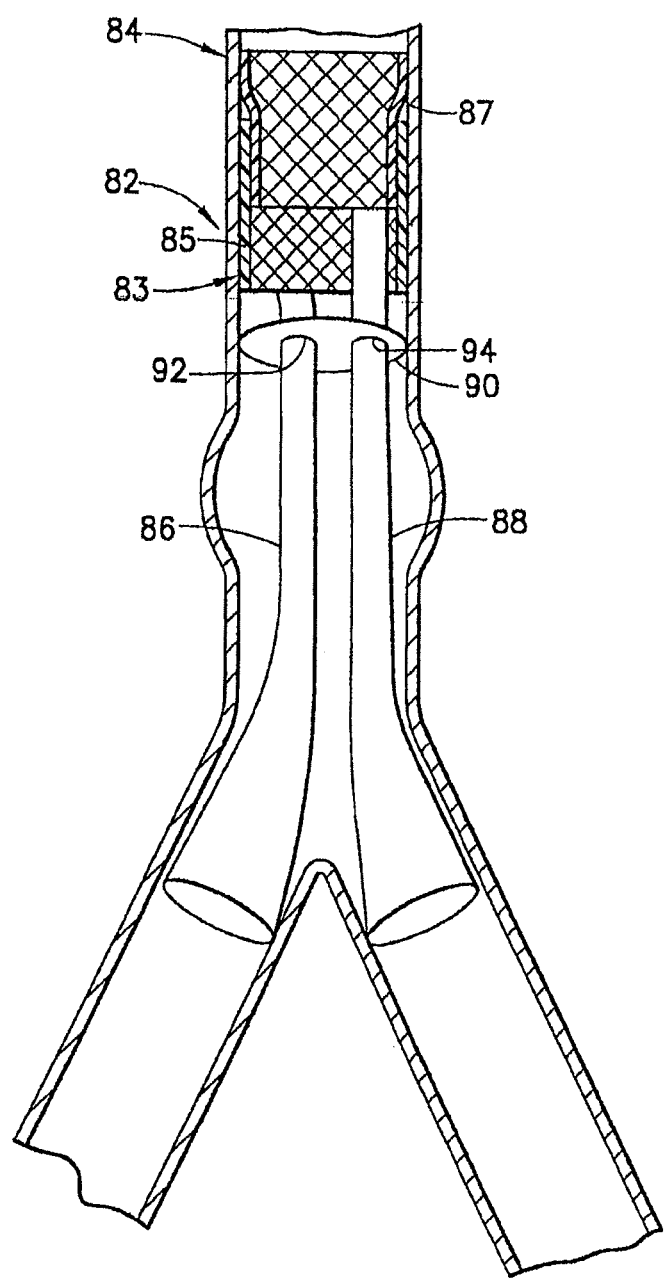
FIG. 16 is a schematic view of a seventh embodiment of an endovascular stent/graft assembly in accordance with the invention.

A seventh embodiment of the endovascular stent/graft assembly of the subject invention is identified generally by the numeral 82 in FIG. 16. The assembly 82 comprises first and second endovascular stent/graft subassemblies 83 and 84. The first subassembly 83 comprises a first stent 85 and a first tubular graft 86. Similarly, the second subassembly 84 comprises a second stent 87 and a second graft 88. The assembly 82 further includes a generally disc-like drum secured in the abdominal aorta 42 at a location upstream of the aneurysm. The drum 90 has first and second mounting apertures 92 and 94 through which portions of the first and second tubular grafts 86 and 88 extend. The extreme upstream ends of the tubular grafts 86 and 88 are secured respectively in end-to-end relationship with the downstream end of the first and second tubular stents 85 and 87, while the downstream ends of the tubular grafts 86 and 88 are disposed respectively in the right and left iliac arteries 40 and 44. The drum or disc 90 prevents blood from flowing around the tubular grafts 86 and 88 and into the region of the aneurysm where blood pressure could cause a rupture of the aneurysm. The stents 85 and 87 provide a secure mounting of the endovascular stent/graft assembly 82 relative to the aneurysm, and prevent any parts of the assembly 82 from migrating downstream due to the pressure of the blood flow. The endovascular stent/graft assembly 82 of FIG. 16 is used in combination with internal stents, such as the internal stent 27 in FIG. 1, that are introduced to the tubular grafts 86 and 88 after complete implantation of portions of the assembly 82 depicted in FIG. 16. Additionally, the assembly 82 may be used in combination with one or two downstream stents, or other fixation devices secured to downstream ends of the respective tubular grafts 86 and 88.

Figure 17:
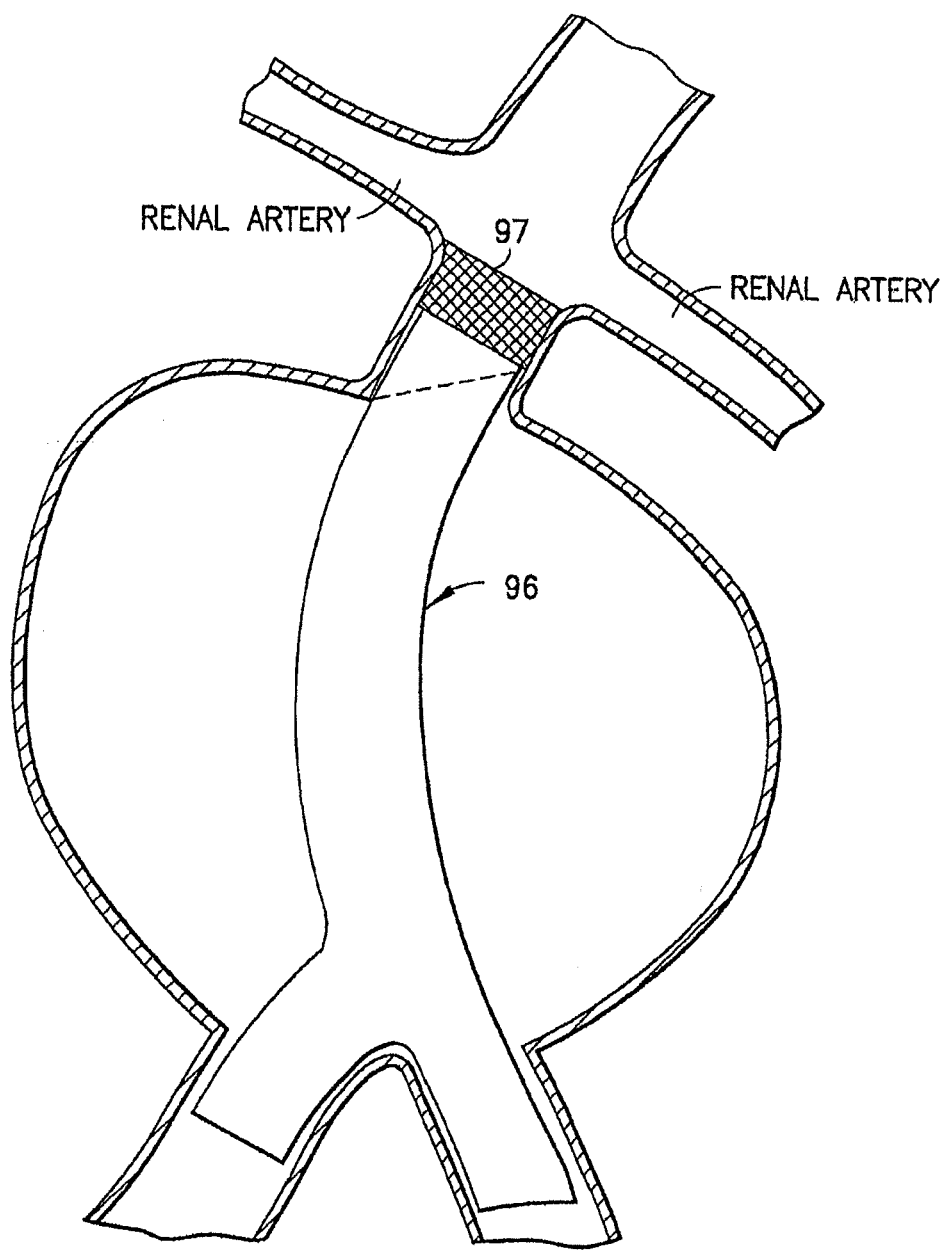
FIG. 17 is a schematic view of an eighth embodiment of an endovascular stent/graft assembly in accordance with the invention.

An eighth embodiment of the endovascular stent/graft assembly of the subject invention is identified generally by the numeral 96 in FIG. 17. The stent/graft assembly 96 is designed in recognition of the fact that somewhat less than half of all patients have a neck defined in the abdominal aorta immediately upstream of the aneurysm. The neck is aligned to the aneurysm at an angle of less than 180°. Endovascular stent/graft assemblies exhibit some flexibility. Thus, a conventional cylindrical endovascular stent/graft assembly can be biased into a noncylindrical curved shape that conforms to the shape of the neck adjacent the aneurysm. However, an initially cylindrical stent/graft assembly with a linear axis of symmetry that is biased into a curved noncylindrical shape will exhibit internal resiliency that will tend to return the stent/graft assembly back to an unbiased cylindrical configuration.

A stent/graft assembly that initially is concentric about a linear axis and then is bent to be concentric about a curved axis will cause portions of the stent/graft assembly on the outside of the curve to circumscribe a smaller arc angle than portions of the stent/graft assembly more inwardly on the curve. As a result, portions of the cylindrical stent/graft assembly that initially are concentric about a linear axis and then are curved to be concentric about a curved axis will be affixed less securely in healthy regions of the blood vessel upstream from the aneurysm and on the outside of the curve of the stent/graft assembly. This configuration is illustrated by the broken line on the endovascular stent/graft assembly 96 shown in FIG. 17. It will be appreciated that even minor shifting of the endovascular stent/graft assembly after implantation can result in catastrophic leaks between the stent/graft assembly and the aneurysm.

To avoid the above-described problems, the endovascular stent/graft assembly 96 shown in FIG. 17 is performed to be unbiased in a curved condition symmetrical about a curved axis. Thus, the stent/graft assembly 96 can be considered to define a section of torus. Additionally, the upstream end 97 is substantially perpendicular to the curved axis of the stent/graft assembly. This requires the stent/graft assembly 96 to be longer on the outside of the curve than on the inside of the curve so that portions of the stent/graft assembly 96 circumscribes substantially equal angles on both inner and outer extremes of the curved stent/graft assembly 96. The curve in the endovascular stent/graft assembly 96 can be achieved by providing longitudinally extending fibers or filaments in the stent and/or the graft that have a preset curve, and aligning the curve filaments, fibers or wires to be substantially parallel with one another. Alternatively, longitudinal extending filaments, fibers or wires on one side of the curve endovascular stent/graft assembly 96 may be shorter than those on the opposite longitudinal side. Still further, a preset unbiased curved can be achieved by appropriate heat treatment of an initially cylindrical stent.

The stent/graft assembly 96 can be biased from its preset curved or toroidal condition back into a substantially cylindrical condition for deployment. This biased cylindrical shape can be maintained by the introducer that is use during deployment. The introducer is removed substantially in the conventional manner after proper positioning of the stent/graft assembly 96. At that time, the stent/graft assembly 96 will be released from its biased cylindrical configuration and will return to its preset unbiased curved or toroidal configuration substantially confirming to the shape imparted by the neck upstream from the aneurysm. The preceding embodiments all relate to stent/graft assemblies where the graft is fixed in substantially end-to-end relationship with the stent. Such a configuration also is acceptable for the stent/graft assembly 96. However, the curved stent/graft assembly 96 also is effective for those situations where the stent and the graft are longitudinally coextensive with one another and where the upstream and downstream ends of both the stent and the graft are at the same or similar axial positions.

Figure 18:
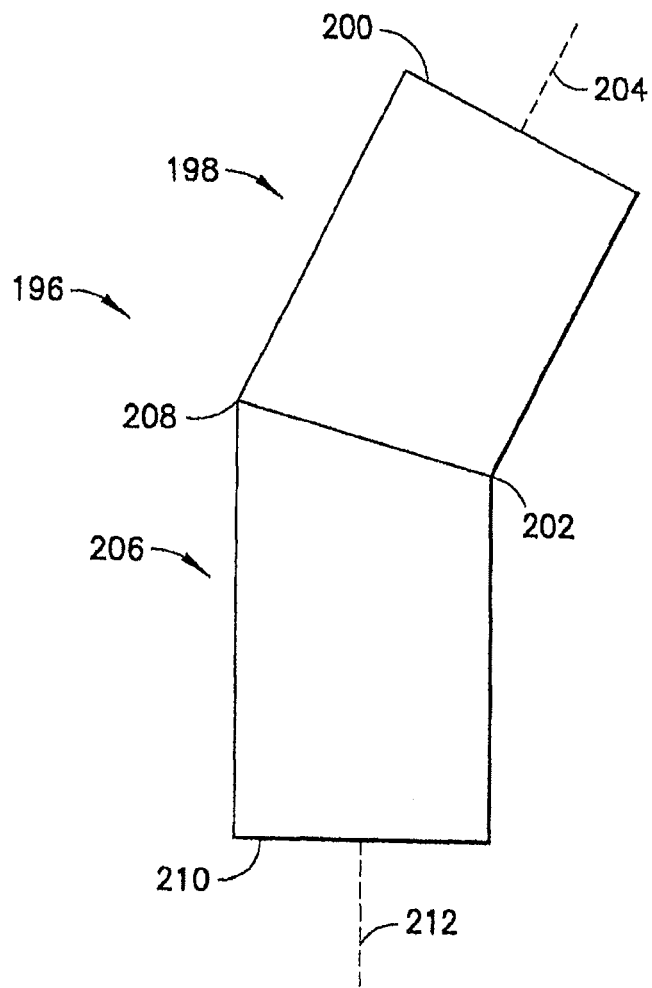
FIG. 18 is a schematic view of a variation of the eighth embodiment.

FIG. 18 shows an angulated endovascular stent/graft assembly 196 that is provided for situations similar to those described above with respect to FIG. 17. The endovascular stent/graft assembly 196 includes a stent 196 with an upstream end 200, a downstream end 202 and a longitudinal axis 204 extending therebetween. The upstream end 200 is aligned substantially orthogonal to the longitudinal axis 204 of the stent 198. The downstream end, however, is not perpendicular to the axis 204, and hence defines a beveled end. The stent/graft assembly 196 further includes a tubular graft 206 having an upstream end 208, and downstream end 210 and an axis 212 extending between the ends. The downstream end 210 is aligned substantially orthogonal to the axis 212. However, the upstream end 208 is not orthogonal to the axis 212. Hence, the upstream end 208 defines a beveled end. The beveled upstream end 208 of the graft 206 is connected substantially and end-to-end relationship with the beveled downstream end 202 of the stent 198. As in the previous embodiments, the end-to-end connection can be achieved by sutures, bonding, adhesive, welding, hooks or the like. Additionally, as with the preceding embodiments, the substantially end-to-end connection may include a small amount of overlap sufficient to achieve the connection. The end-to-end connection of the beveled ends 202 and 208 of the stent 198 and the graft 206 respectively creates a bend that can more nearly approximate the shape of the blood vessel adjacent the angulated neck upstream of the aneurysm. This alternate embodiment provides certain practicalities over the embodiment of FIG. 17. For example, the angle of bend can be controlled precisely by effectively mitering the ends at an appropriate angle. Second, insertion can be easier than with a stent/graft assembly that is curved along its length. In this latter regard, it will be appreciated that the graft 206 is very flexible and during insertion will collapse and readily follow the stent 198 as the stent 198 is inserted generally along its axis 204.

Figure 19:
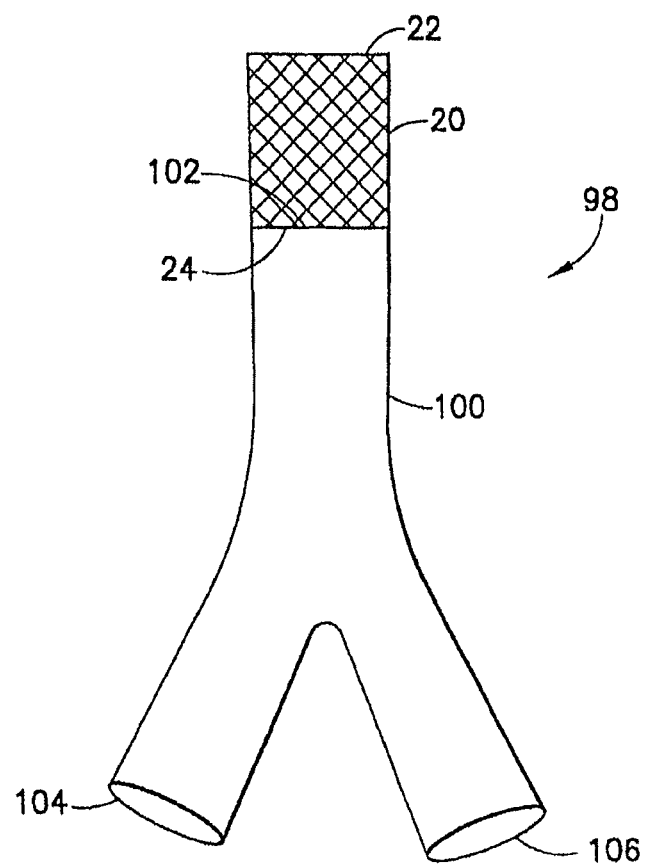
FIG. 19 is a schematic view of a modular endovascular stent/graft assembly that represents a ninth embodiment of the invention intended primarily for deployment into the abdominal aorta and adjacent regions of the left and right iliac arteries.

FIG. 19 shows an endovascular stent/graft assembly 98 with a stent 20, substantially identical to the stents 20 described and illustrated above. More particularly, the stent 20 of the assembly 98 in FIG. 19 has opposed upstream and downstream ends 22 and 24. The assembly 98 includes a one piece bifurcated graft 100. The graft 100 includes an upstream end 102 that is fixed in substantially end-to-end axial engagement with the downstream end 24 of the stent 20. Additionally, the graft 100 includes two downstream legs 104 and 106 for disposition respectively in the right and left iliac arteries 40 and 44. The one piece bifurcated graft 100 of FIG. 19 eliminates some of the intraoperative assembly required with the modular system of FIG. 15. The bifurcated graft 100 is used with one or more internal stents that are deployed after insertion substantially as described with respect to the other embodiments. Additionally, downstream stents can be affixed to either of the downstream legs 104 and 106.

Variations of the FIG. 19 embodiment also may be provided. For example, more than two legs may be provided. Furthermore the stent 20 may have branches intermediate its length, and tubular grafts may be connected in substantially end-to-end relationship with the branches of the stent.

Figure 20:
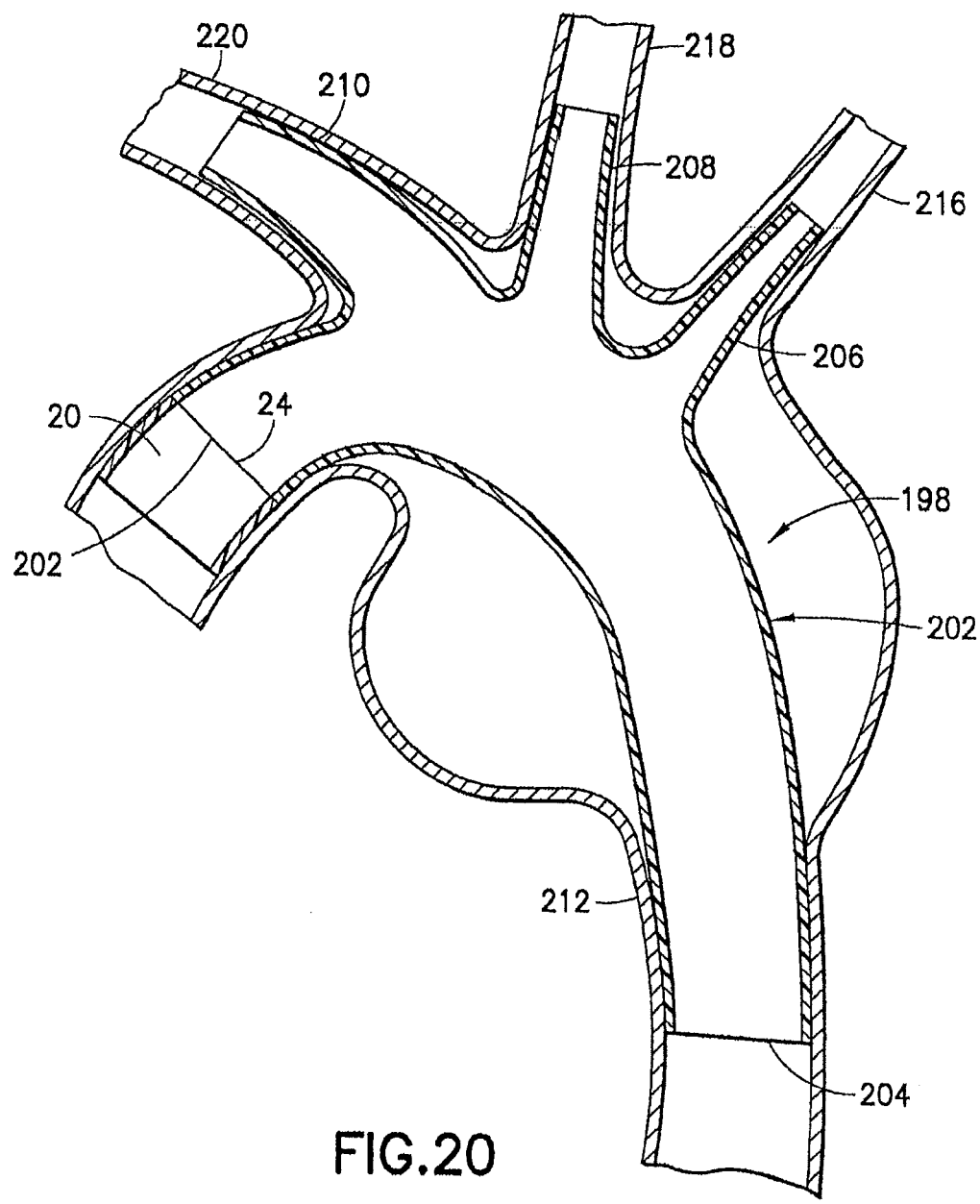
FIG. 20 is a schematic view of a variation of the stent/graft assembly of FIG. 19.

An example of a variation of the FIG. 19 embodiment is illustrated in FIG. 20. In particular, FIG. 19 shows an endovascular stent/graft assembly 198 with a stent 20 identical to the stent 20 described and illustrated above. The assembly 198 includes a graft 200 with a tubular upstream end 202 connected to the downstream end 24 of the stent 20. The graft 200 also has a tubular downstream end 204 and three tubular branches 206, 208 and 210 extending transversely from intermediate positions along the graft 200. FIG. 20 shows the endovascular stent/graft assembly 198 deployed for treating an aneurysm of the thoracic aorta 212. The tubular branches 206, 208 and 210 extend to arteries that branch from the thoracic aorta 212, including the left subclavian artery 216, the left carotid artery 218 and the brachiocephalic artery 220.

Figure 21:
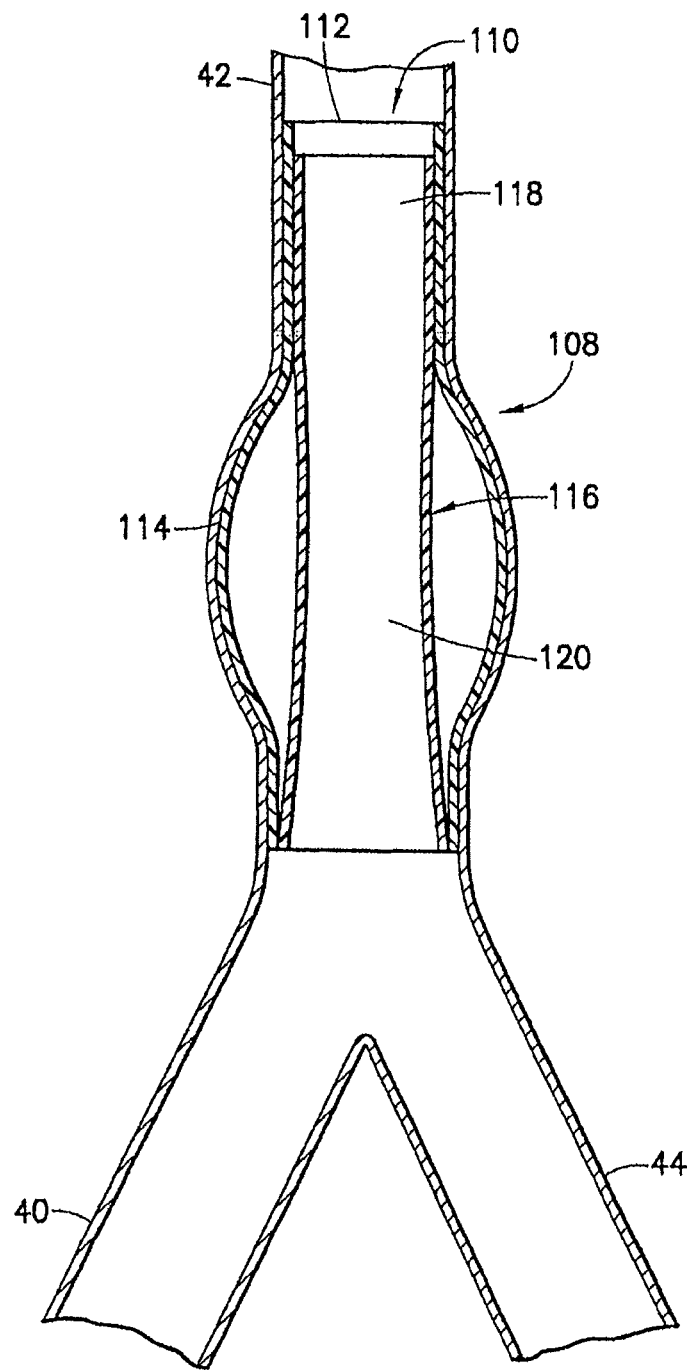
FIG. 21 is a schematic view of a tenth embodiment of an endovascular stent/graft assembly in accordance with the invention.

In many instances, small blood vessels will communicate with portions of the abdominal aorta that have the aneurysm. Blood delivered by these blood vessels can increase pressure between the aneurysm and the graft. Such pressure can lead to a rupture of the aneurysm and/or damage to the graft. The endovascular graft assembly 108 of FIG. 21 is specifically configured to occlude small side blood vessels that lead into the aneurysm. More particularly, the assembly 108 includes an outer stent/graft subassembly 110 that comprises an upstream tubular stent 112 and a downstream expandable graft 114. The stent 112 and graft 114 are connected in substantially end-to-end axial alignment as described and illustrated with respect to the other embodiments herein. The downstream graft 114 of the outer stent/graft subassembly 110 differs from the tubular grafts described and illustrated above. More particularly, the outer graft 114 may be a synthetic fabric or a detachable balloon that has been used in the prior art. Specifically, the outer graft 114 can be expanded radially to conform substantially to the shape of the aneurysm and to thereby occlude the small blood vessels that lead into the aneurysm. The assembly 108 further includes an inner stent/graft subassembly 116 that has an upstream stent 118 and a downstream tubular graft 120. The inner subassembly 116 may be substantially identical to the endovascular stent/graft assembly 10 described with respect to FIG. 1 and other embodiments set forth above. Thus, the tubular graft 120 of the inner subassembly 116 is not expandable. An inner stent similar to the inner stent 27 described and illustrated above may extend through the tubular graft 120. The space between the inner and outer graft 114 and 120 may be filled with blood, a contrast liquid, an adhesive or water. Variations of this embodiment may include a detachable balloon between the inner graft 120 and the expandable outer graft 114. Alternatively, the detachable balloon may make the separate inner graft unnecessary. Still further, the detachable balloon may make a separate internal stent for the outer graft unnecessary.

Figure 22:
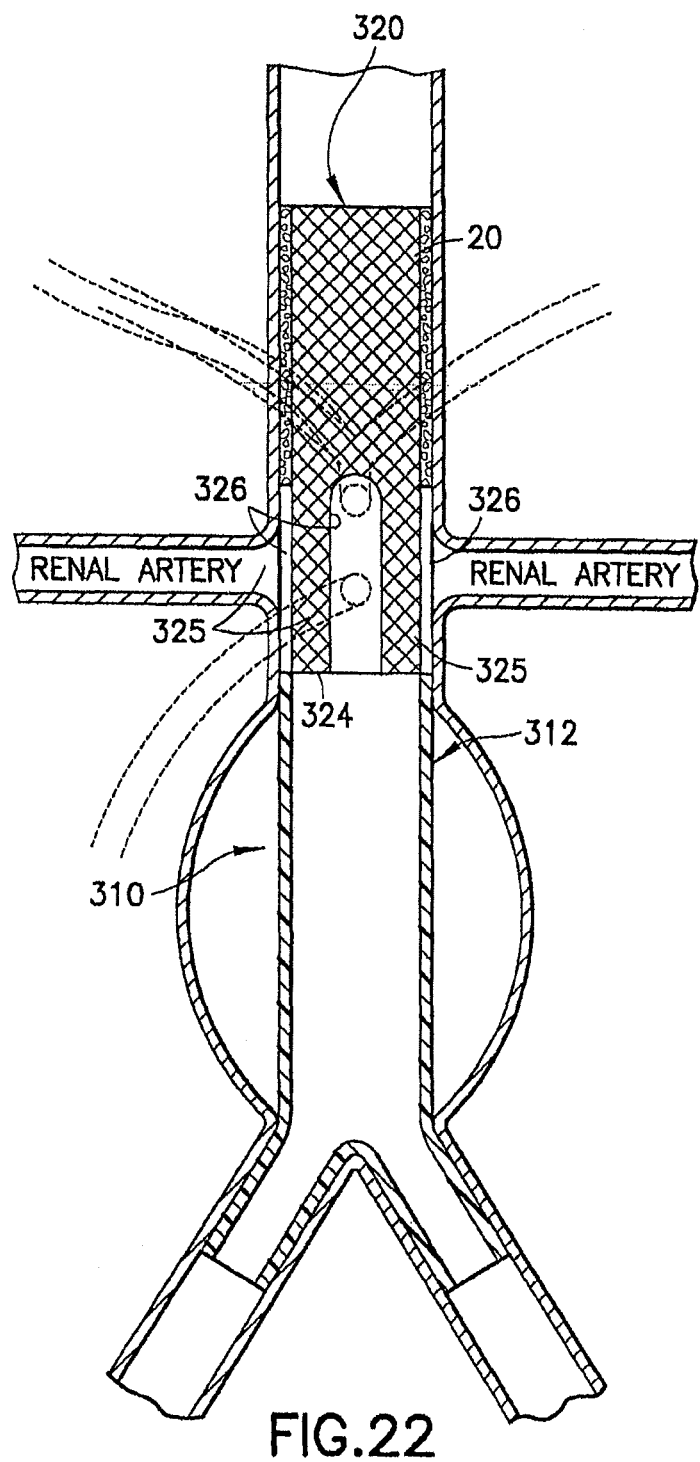
FIG. 22 is a schematic view of an eleventh embodiment of an endovascular stent/graft assembly in accordance with the invention.

FIG. 22 shows a stent/graft assembly 310 that incorporate features of the assemblies shown in FIGS. 1-4B. In particular, the stent/graft assembly 310 includes a graft 312 and a stent 320 that are connected substantially in end-to-end relationship. As in the preceding embodiment, the stent 20 is intended for disposition adjacent a healthy section of the blood vessel upstream from a aneurysm. The tubular graft 312 typically will extend downstream from the stent 320 across an aneurysm and into a location downstream from the aneurysm. However, many such aneurysms occur in the abdominal aorta slightly downstream from the renal arteries. The stent 320 often will take the form of a tubular wire mesh that normally should permit a blood flow through the tubular mesh and into the renal arteries. However, the tubular mesh of the stent 320 can become blocked by materials flowing in the blood. Blockage of the renal arteries can lead to kidney failure and is more likely to occur with the wire mesh stent in place than without the wire mesh. Hence, the implantation of the stent/graft assembly 10 of FIG. 1 in the abdominal aorta with the stent 320 aligned with the renal arteries could overcome the problems associated with the aneurysm, but could cause kidney problems due to blockage of the renal arteries. The FIGS. 4A and 4B embodiments provide one solution to that problem. FIG. 22 provides another solution without the use of the connecting wires of FIGS. 4A and 4B. In particular, the stent 320 of FIG. 22 has a downstream end 324 defined by a plurality of crenulations 325 that are separated by cutouts 326 that extend axially a sufficient distance to overlap the renal arteries and visceral arteries. The crenulations 325 at the downstream end 324 of the stent 320 are affixed in substantially end-to-end relationship with the upstream end of the tubular graft 312. The axially extending cutouts 326 permit unimpeded blood flow to the renal arteries and visceral arteries.

Figure 23:
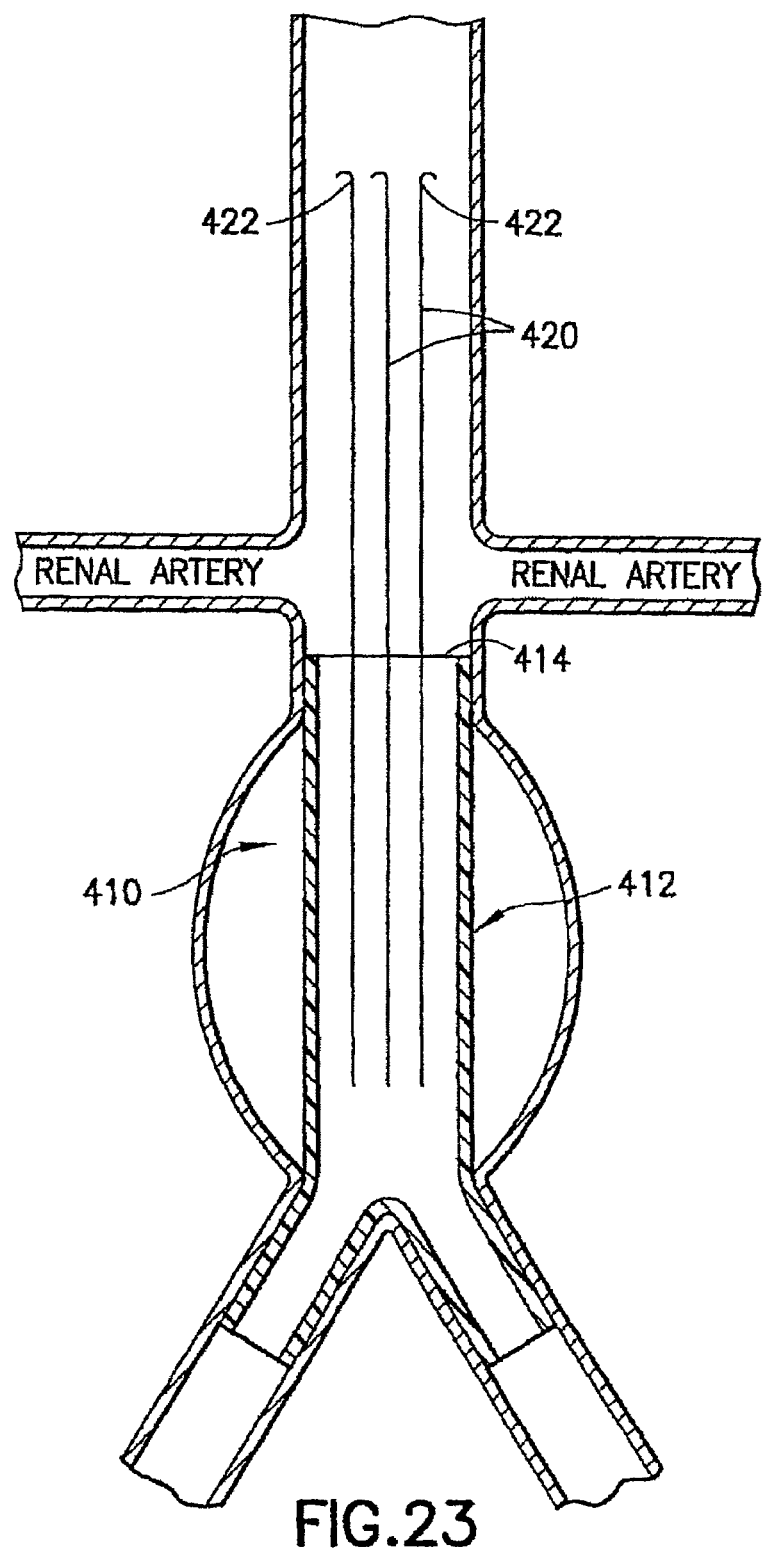
FIG. 23 is a schematic view of a twelfth embodiment of an endovascular stent/graft assembly in accordance with the invention.

FIG. 23 shows still a further alternative embodiment that may be adopted as an alternate to the embodiments of FIG. 4B and FIG. 22. In particular, the assembly 410 in FIG. 23 includes a tubular graft 412 with an upstream end 414 and opposite downstream ends 416 positioned in the iliac arteries. The assembly 410 further includes wires 420 extending at least partly through the graft 412 and projecting upstream therefrom. Assembly 410 does not have a tubular stent comparable to the tubular stent 20 shown in FIGS. 4A and 4B. Rather, the upstream ends of the wires 420 are formed with hooks or barbs 422 that permit anchoring of the assembly 410 in a healthy section of a blood vessel that may be upstream from the aneurysm. The embodiment of FIG. 23 also is well suited for treatment of an aneurysm in the abdominal aorta. In particular, the upstream end 414 of the graft 412 can be positioned between the aneurysm and the renal arteries. The wires 420 extend to locations in the abdominal aorta upstream from the renal arteries and upstream from the visceral arteries. Thus, as in the embodiments shown in FIGS. 4B and 22, blood flow to the renal arteries and the visceral arteries is substantially unimpeded.

Figure 24:
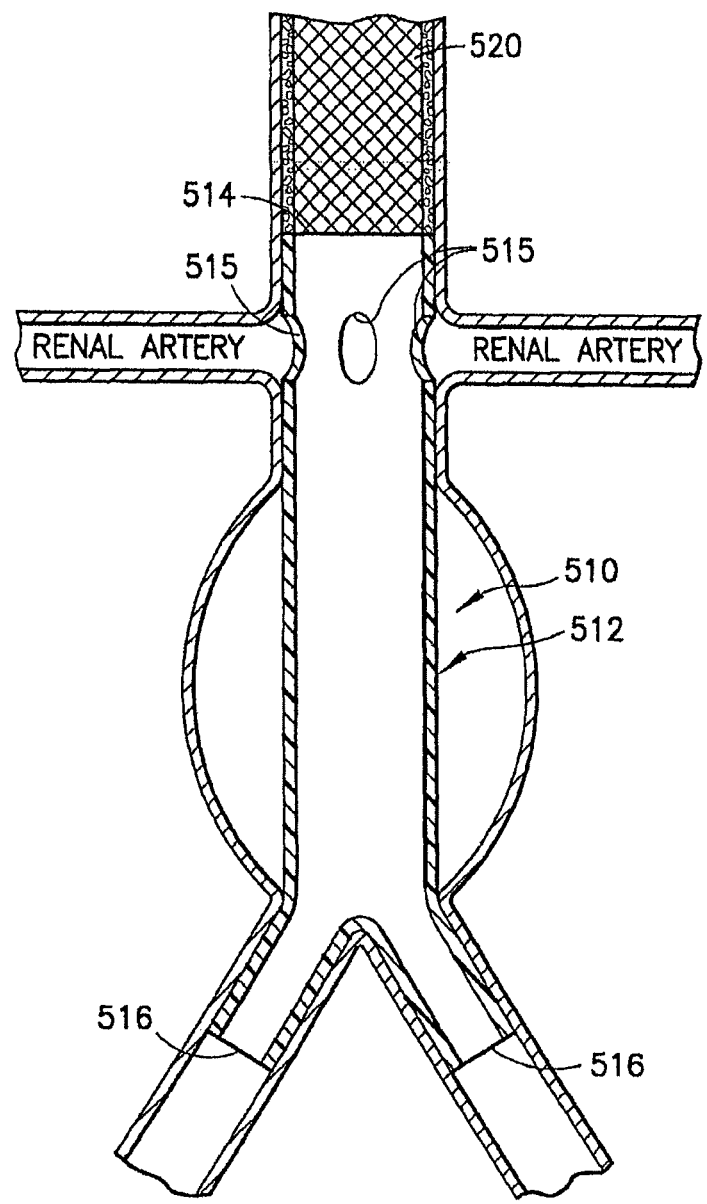
FIG. 24 is a schematic view of a thirteenth embodiment of an endovascular stent/graft assembly in accordance with the invention.

FIG. 24 shows still another embodiment that may be adopted as an alternate to the embodiments of FIGS. 4B, 22 and 23. In particular, the assembly 510 in FIG. 24 includes a tubular graft 512 with an upstream end 514 and opposite downstream ends 516 positioned in the iliac arteries. The assembly 510 further includes a tubular stent 520 connected to the upstream end 514 of the tubular graft 512 in substantially end-to-end relationship. In the illustrated embodiment, the tubular stent 520 is positioned in the abdominal aorta at a location upstream from the renal arteries. Apertures 515 are formed in portions of the tubular graft 512 near the upstream end 514 to permit a flow of blood to the visceral arteries and the renal arteries. However, portions of the tubular graft 512 closer to the downstream ends 516 are substantially free of apertures. As illustrated in FIG. 24, these portions of the tubular graft 512 without the apertures bridge the aneurysm.

Figure 25:
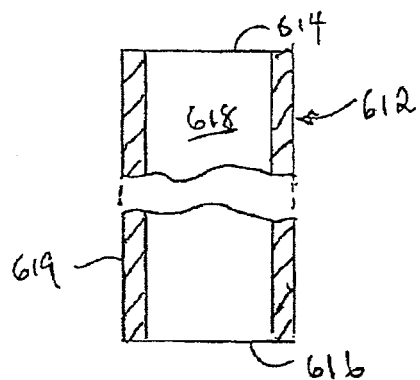
FIG. 25 is a schematic view of a graft in a first orientation for use in a stent/graft assembly of a fourteenth embodiment of the invention.
Figure 26:
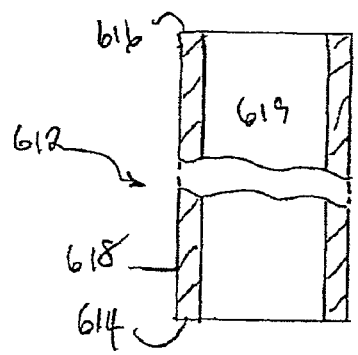
FIG. 26 is a schematic view of the graft of FIG. 25 in a second orientation.

FIGS. 25-29 show a stent/graft assembly 610 that may be similar to any of the previously described embodiments but that is oriented differently prior to deployment and then deployed differently. In particular, the assembly 610 includes a tubular graft 612 with opposite longitudinal ends 614 and 616. The graft 612 further includes an inner circumferential surface 618 and an outer circumferential surface 619, as shown in FIG. 25. The graft 612 then is turned inside out, as shown in FIG. 26 so that the initial inner circumferential surface 618 faces outwardly and so that the initial outer circumferential surface 619 faces inwardly. In this regard, it is understood that the graft 612 is formed from thin flexible material, and the manipulation to convert the graft 12 from the FIG. 25 orientation to the FIG. 26 orientation is roughly comparable to the manipulation carried out to fold a pair of socks.

Figure 27:
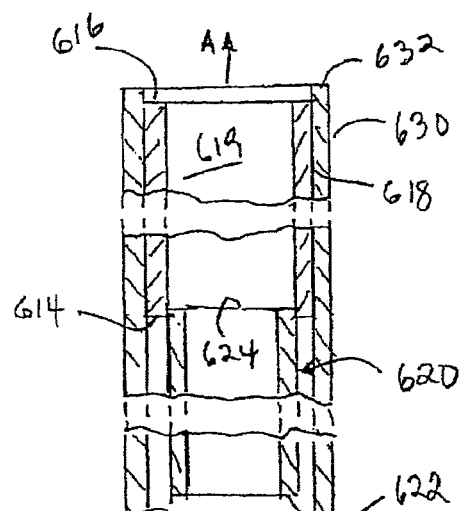
FIG. 27 is a schematic view of the fourteenth embodiment of the invention during an initial phase of deployment.
Figure 28:
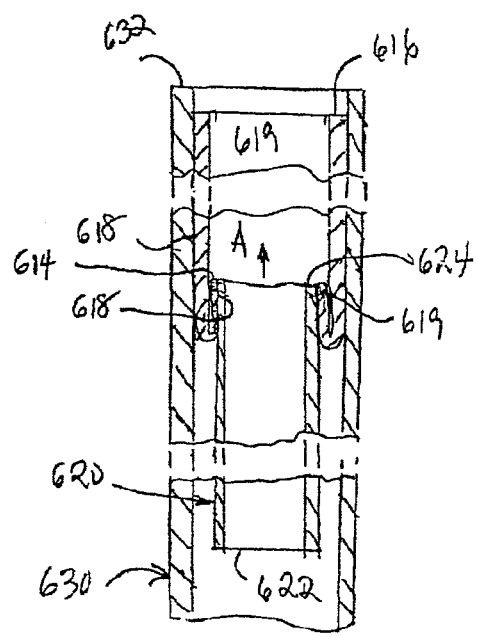
FIG. 28 is a schematic view of the fourteenth embodiment at a later stage of deployment.

FIG. 27 shows the graft 612 in the FIG. 26 orientation connected in substantially end-to-end relationship with a stent 620 and disposed within a substantially conventional tubular introducer sheath 630. More particularly, the stent 620 has a free end 622 and a connected end 624 that is connected in substantially end-to-end relationship with the end 614 of the tubular graft 612. The free end 616 of the tubular graft 612 is releasably connected near the end 632 of the introducer sheath 630. The releasable connection may be achieved with sutures or other known connection means that would be appreciated by those skilled in this art. The introducer sheath 630 is advanced to an appropriate location in a blood vessel in a direction indicated by the arrow A in FIG. 27. Thus, the tubular graft 612 is in a leading position during this deployment.

Figure 29:
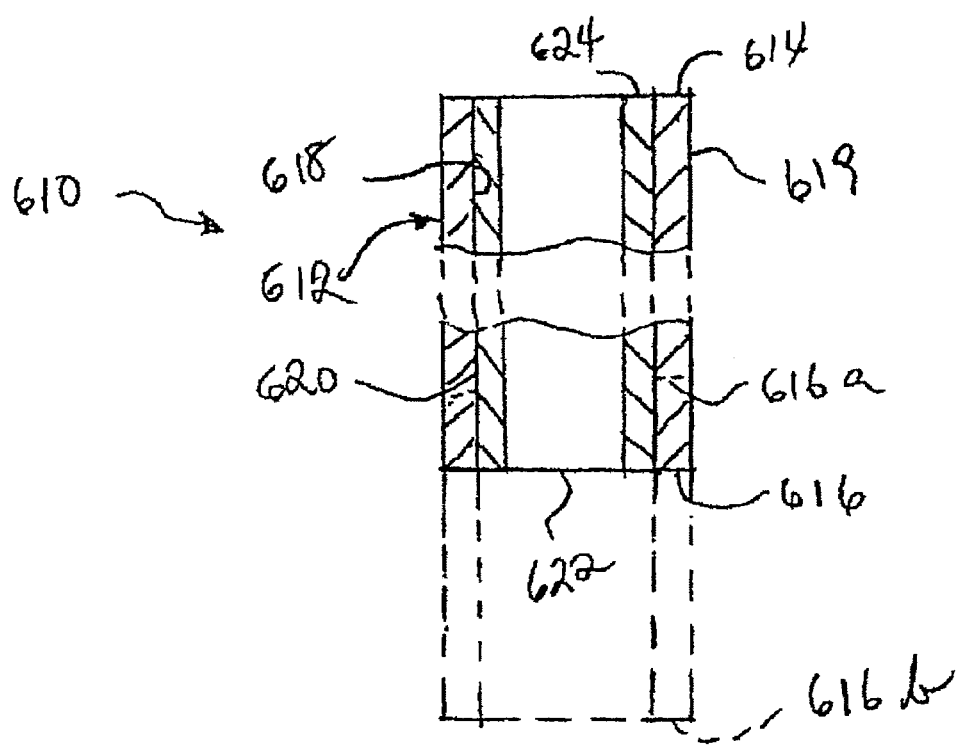
FIG. 29 is a schematic view of the fourteenth embodiment after complete deployment.

Movement of the introducer sheath 630 in the direction A is stopped when the stent/graft assembly 610 is at an appropriate position relative to the aneurysm or other vascular anomaly. The stent 620 then is advanced in the direction of the arrow A while keeping the graft 612 and the introducer sheath 630 substantially stationary. This movement is illustrated schematically in FIG. 28 and begins reversing the graft 612 back into the FIG. 25 orientation. This movement of the stent 620 stops in FIG. 29 when the graft 612 has been completely reverted back to the FIG. 25 orientation. Thus, the circumferential surface 618 faces inwardly and the circumferential surface 619 faces outwardly. FIG. 29 shows that the end 624 of the stent 620 is connected in substantially end-to-end relationship with the end 614 of the graft 612, and hence substantially in conforms with the preceding embodiments. The solid line depiction of FIG. 29 shows the free ends 622 of the stent 620 substantially aligned with the free end 616 of the tubular graft 612. However, the numeral 616*a* shows a variation where the free end 622 of the stent 620 extends axially beyond the free 616*a* of the graft 612. This orientation reflects the fact that there may be better direct affixation of the stent 620 to the blood vessel. The broken line depiction in FIG. 29 shows a variation where the free end 616*b* of the graft 612 extends axially beyond the free end 622 the stent 620. This latter variation may require a subsequent deployment of an internal stent to support portions of the graft 612 near the free end 616*b*.

The stent/graft assembly 610 illustrated in FIGS. 25-29 achieves a small cross section during deployment, as described with respect to the previous embodiments. Additionally, the stent/graft assembly 610 of FIGS. 25-29 can eliminate or reduce the need for internal stents, and hence substantially shortens and simplifies the surgical deployment of the stent/graft assembly 610.

Figure 30:
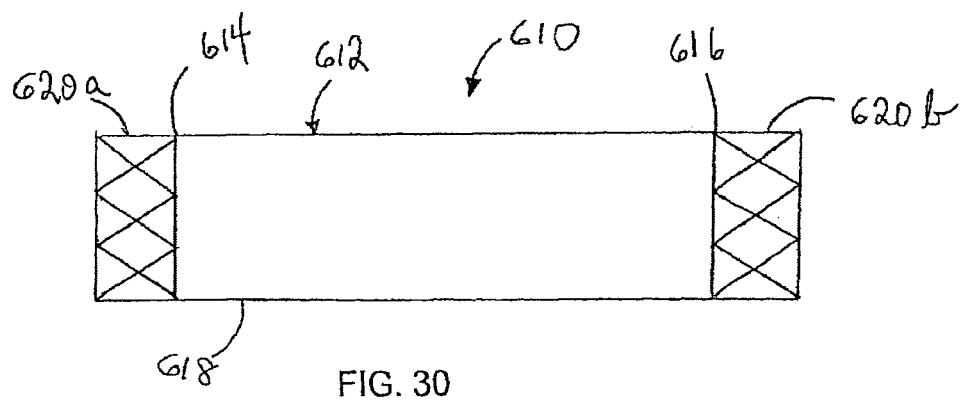
FIG. 30 is a schematic view of the fifteenth embodiment of the invention prior to deployment.
Figure 31:
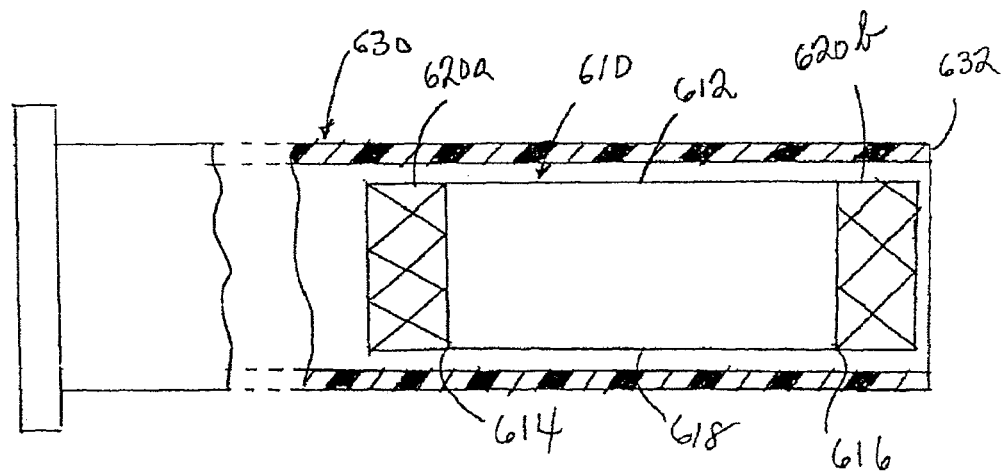
FIG. 31 is a schematic view of the fifteenth embodiment in an introducer sheath.
Figure 32:
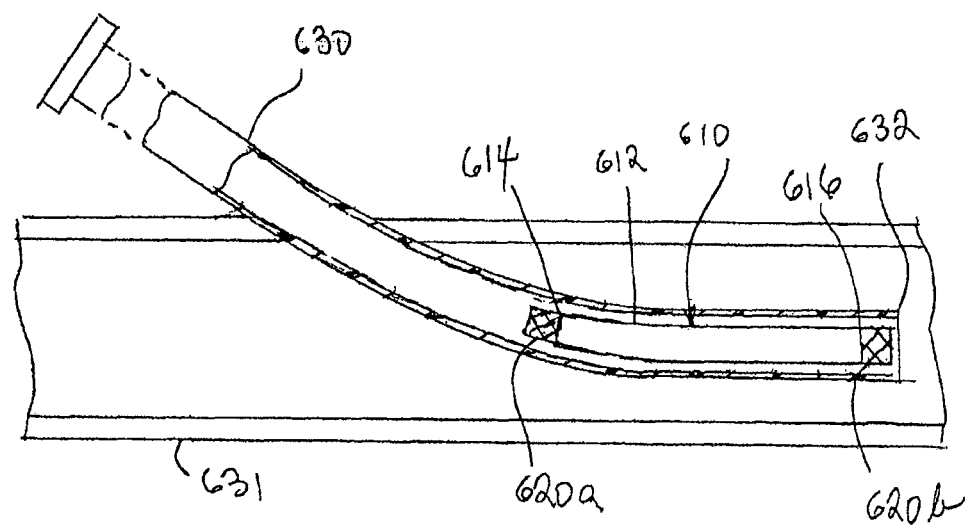
FIG. 32 schematically illustrates the introducer sheath and the stent/graft assembly of FIG. 30 being introduced into a blood vessel.
Figure 33:
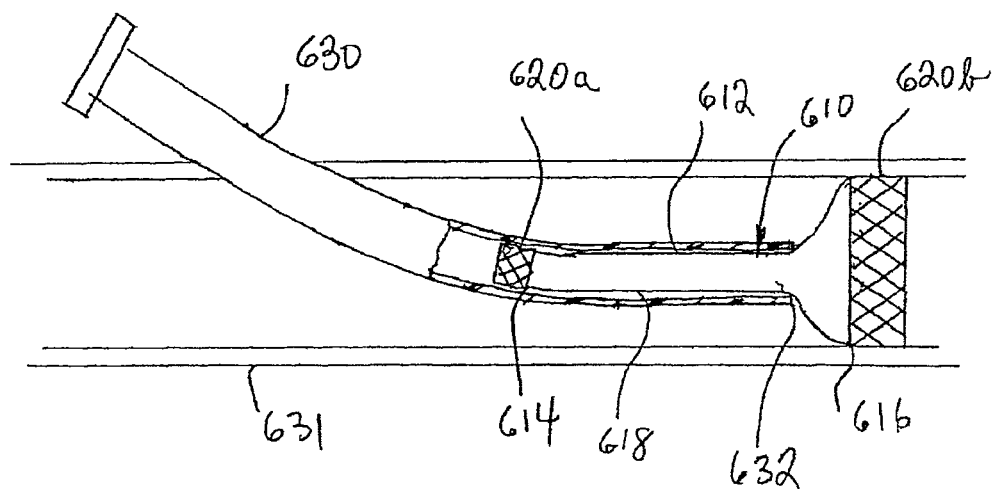
FIG. 33 is a schematic view at a first stage of deployment of the stent/graft assembly of FIG. 30.
Figure 34:
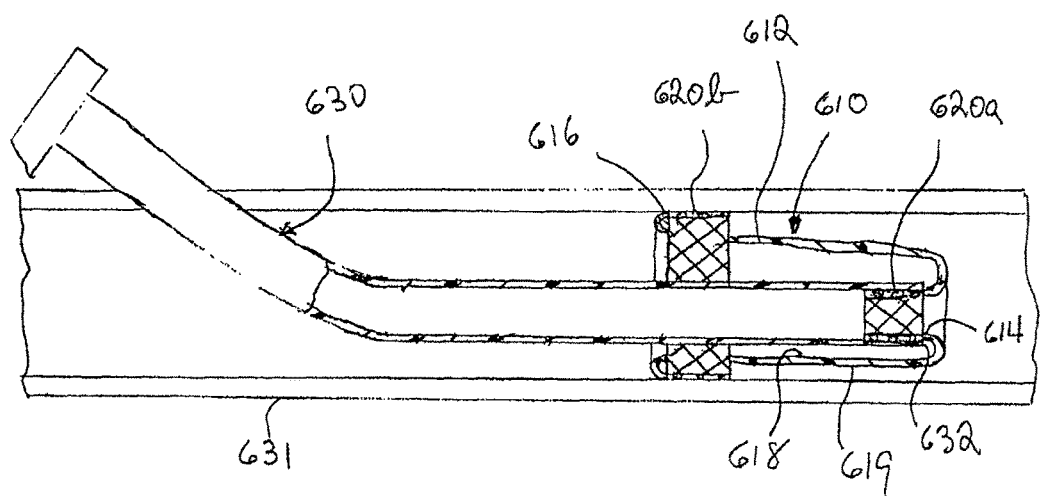
FIG. 34 is a schematic view at a second stage of deployment of the stent/graft assembly of FIG. 30.
Figure 35:
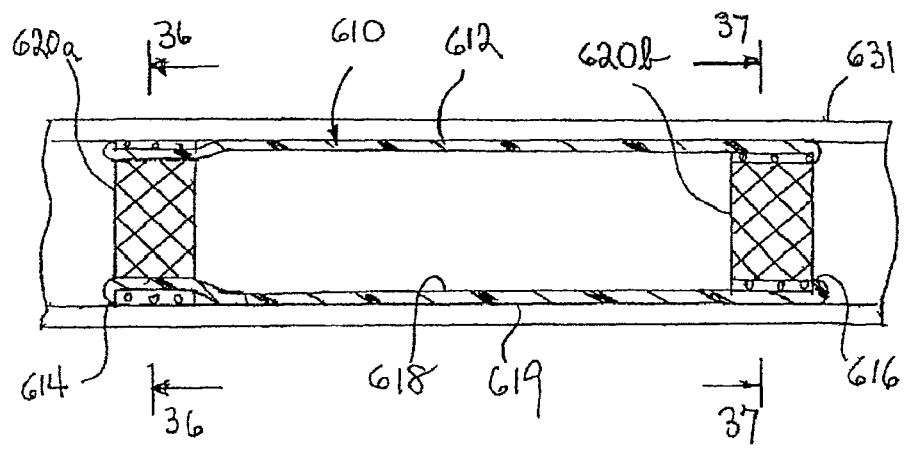
FIG. 35 is a schematic view at a final stage of deployment of the stent/graft assembly of FIG. 30.
Figure 36:
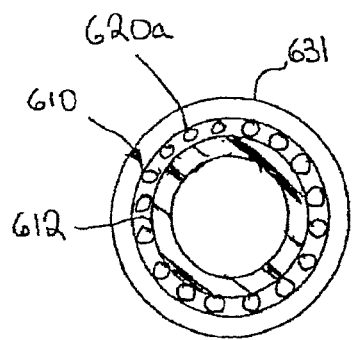
FIG. 36 is cross-sectional view taken along lines 36-36 in FIG. 35.
Figure 37:
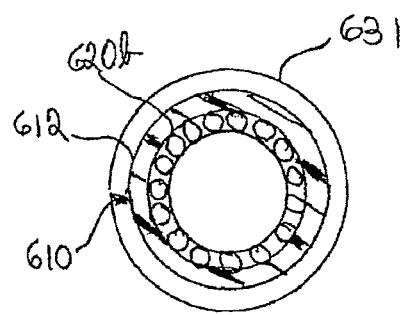
FIG. 37 is a cross-sectional view taken along lines 37-37 in FIG. 35.

Deployment of the stent/graft assembly 610 can be facilitated by opening the graft 612 to its full diameter prior to inverting the stent/graft assembly 610. A first approach for achieving this opening of the graft 612 can be achieved by employing first and second stents 620*a* and 620*b* fixed respectfully in end-to-end relationship to opposite ends 614 and 616 of the graft 612, as shown in FIGS. 30-37. The graft 612 initially is inverted, as shown in FIG. 26, so that the inner surface 618 faces out. The collapsed stents 620*a* and 620*b* then are secured to opposite ends 614 and 616 of the graft 612 to define a stent/graft assembly 610, as shown in FIG. 30. The stent/graft assembly is positioned in an introducer sheath 630 as shown in FIG. 31. The introducer sheath 630 is moved through the artery 631, as shown in FIG. 32, and is positioned at an appropriate location near a diseased section of the artery. The stent 620*b* then is advanced slightly beyond the axial end 632 of the introducer sheath 630 and is expanded, as shown in FIG. 33, by known expansion means, such as expansion means used in known self-expanding stents. The expansion of the stent 620*b*, as shown in FIG. 33 will permit the unexpanded stent 620*a* and portions of the graft 612 attached thereto to be moved into and through the expanded stent 620*b*, as shown in FIG. 34. As a result, the graft 612 is reinverted so that the outer surface 619 is turned to gradually face out. The stent 620*a* is moved to an appropriate position on the artery 631 spaced from the stent 620*b*. The stent 620*a* then is expanded into supporting engagement with the interior surface of the artery 631, as shown in FIGS. 35-37. In this deployed condition, the graft 612 extends from the end of the stent 620*b* furthest from the stent 620*a*. The graft 612 then is disposed against the outer circumferential surface of the stent 620*b* and continues through the blood vessel to the end of the stent 620*a* farthest from the stent 620*b*.

Figure 38:
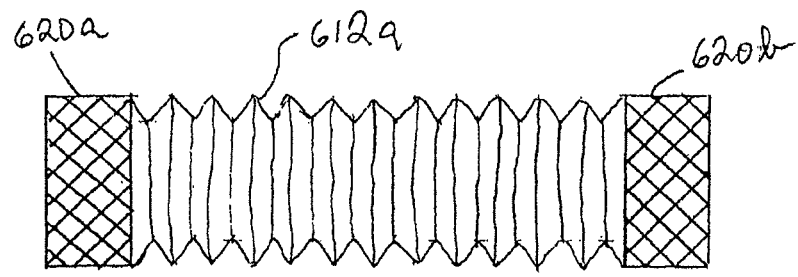
FIG. 38 is a schematic view of a sixteenth embodiment that is similar to the fifteenth embodiment but employs a corrugated graft.

The length of the graft 612 should be sufficient to bridge the diseased section of the artery. However, decisions regarding the disposition of the stents 620*a* and 620*b* and hence the length of the graft 612 may be made intraoperatively. To facilitate such intraoperative decisions, a corrugated graft 612*a* may be employed with the stents 620*a* and 620*b* as shown in FIG. 38. This assembly of the corrugated graft 612*a* and the stents 620*a* and 620*b* are deployed in exactly the manner described above and shown in FIGS. 30-37. However, the corrugations in the graft 612*a* permit variations in the length of the graft 612*a*. Corrugated grafts of this type are known to those skilled in the art and have been used in other situations. Corrugated grafts are shown, for example, in published U.S. Patent Application No. US2003/0088305.

Figure 39:
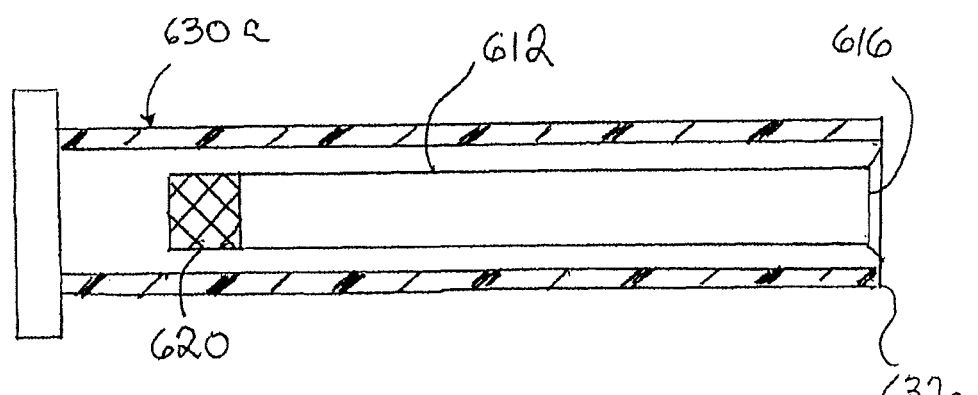
FIG. 39 is a schematic view of a seventeenth embodiment showing a stent/graft assembly disposed in an introducer sheath.
Figure 40:
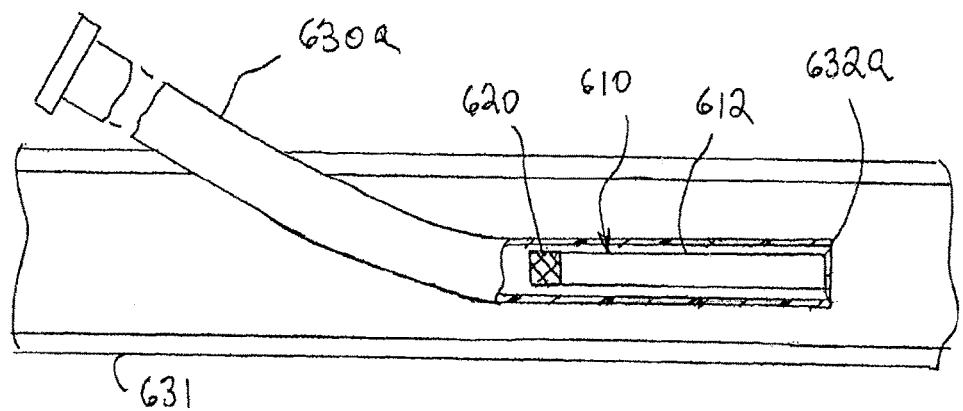
FIG. 40 is a schematic view of the seventeenth embodiment at an initial stage of deployment into a blood vessel.
Figure 41:
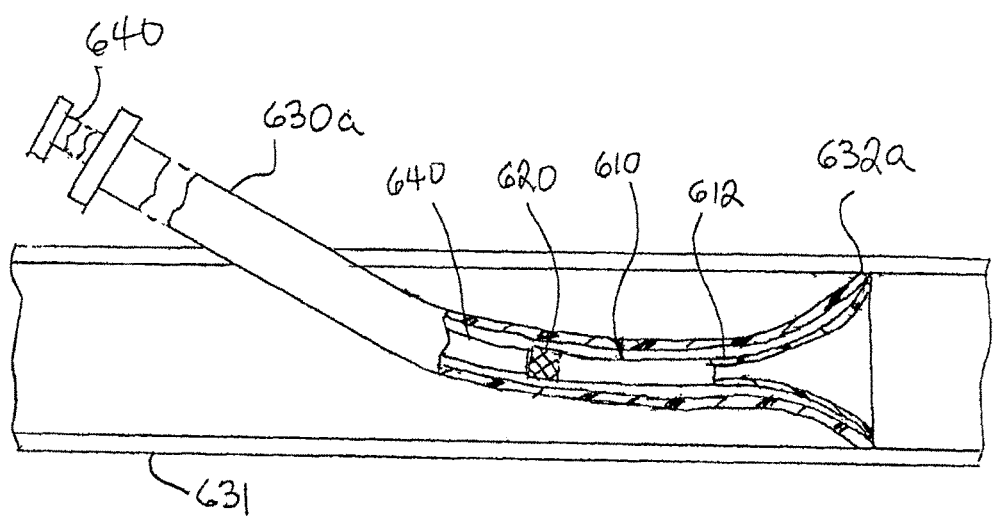
FIG. 41 is a schematic view similar to FIG. 40 but showing the stent/graft assembly at a second phase of deployment.
Figure 42:
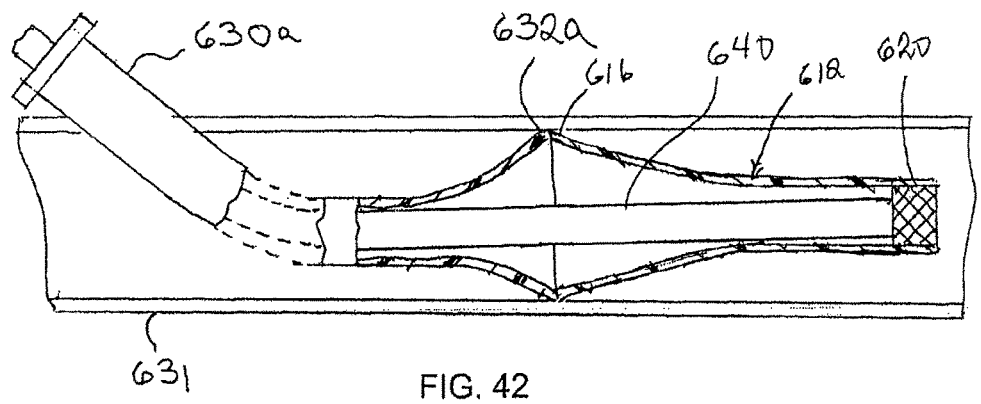
FIG. 42 is a schematic view similar to FIG. 40 but showing the stent/graft assembly at a third phase of deployment.
Figure 43:
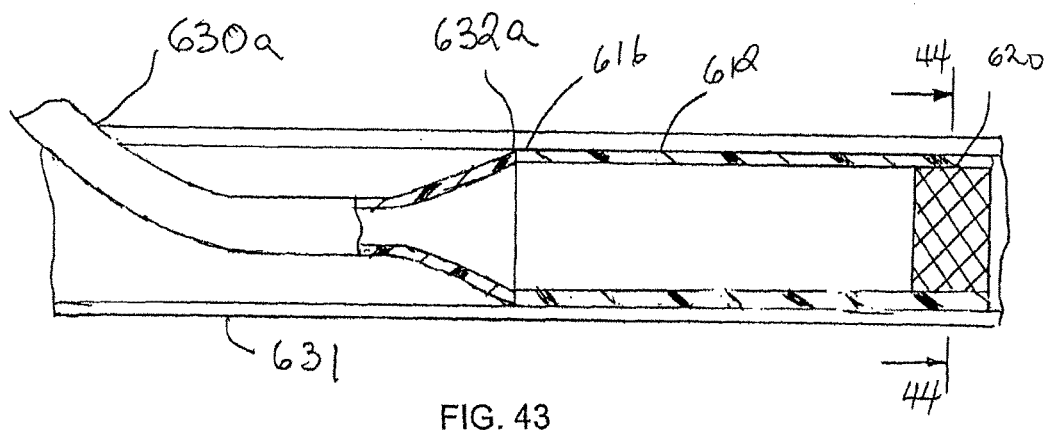
FIG. 43 is a schematic view similar to FIG. 40 but showing the stent/graft assembly at a fourth phase of deployment.
Figure 44:
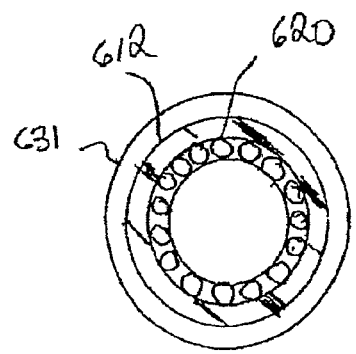
FIG. 44 is a cross-sectional view taken along lines 44 in FIG. 43.
Figure 45:
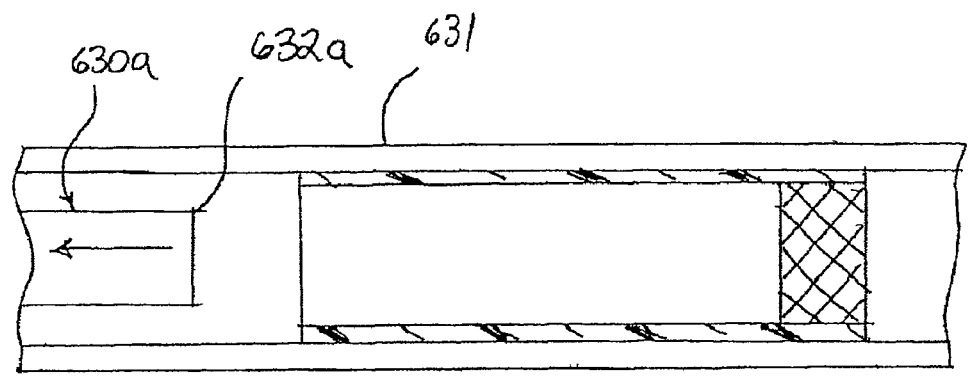
FIG. 45 is a schematic view showing the stent/graft assembly of FIG. 39 after deployment.

The graft 612 can be opened without the use of the above-described second stent 620*b*. More particularly, the above-described end-to-end assembly of the graft 612 and the stent 620 can be used with an expandable introducer sheath 630*a*, as shown in FIGS. 39-45. An expandable introducer sheath is known in the art for use other than the use disclosed herein. A typical expandable introducer sheath is shown published U.S. patent applications, including Publication No. US2004/0082962, Publication No. 2004/0039435 and Publication No. 2004/0010280. In this embodiment, the end 616 of the graft 612 opposite the stent 620 is temporarily and releasably connected to the free end 632*a* of an expandable introducer sheath 630*a*, as shown in FIG. 39. The introducer sheath 630*a* then is advanced through the artery to the selected location near the diseased section of the blood vessel, as shown in FIG. 40. The end 632*a* of the expandable introducer sheath 630 then is expanded, as shown in FIG. 41, thereby causing the end 616 of the graft 612 to expand as well. The stent 620 and portions of the graft 612 attached to the stent 620 then are advanced by a pusher catheter 640 axially through the expanded end 632*a* of the introducer sheath 630*a* and through the opened end of the graft 612 as shown in FIG. 42. The stent 620 then is expanded (FIG. 43) and urges the graft 612 out against the wall of the blood vessel, as shown in FIGS. 43 and 45. The introducer sheath 630*a* then is separated from the graft 612 and withdrawn (FIG. 45).

Figure 46:
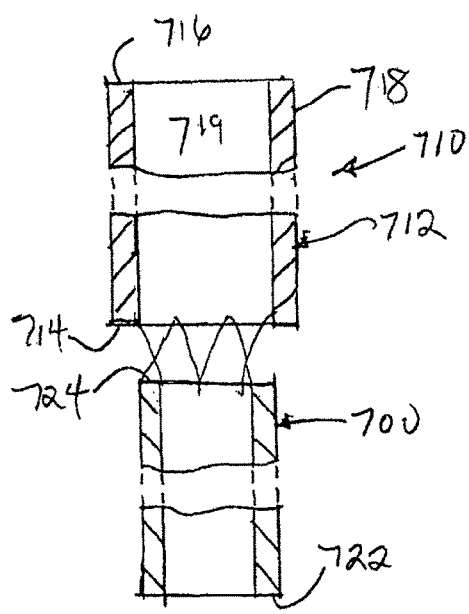
FIG. 46 is a schematic view of an eighteenth embodiment during deployment.

As noted above, the substantially end-to-end affixation between the stent and the graft can include an axial space between the stent and the graft. Such a space can be applied to the embodiment of the invention depicted in FIGS. 25-41. In this regard, the stent/graft assembly 700 of FIG. 46 shows a graft 712 with a connected end 714 and a free end 716. The graft 712 is inverted from its pre-deployment configuration so that the initial outer circumferential surface 619 faces in and so that the initial inner circumferential surface 618 faces out. The stent/graft assembly 700 further includes a stent 720 with a free end 722 and a connected end 724. The connected end 724 of the stent 720 is connected to the connected end 714 of the graft 720 by sutures 715 or other means known to those skilled in the art that provide an axial gap between the connected ends 714 and 724.

The stent/graft assembly 700 is deployed substantially in the same manner as the assembly 600 described above. After proper positioning, the stent 720 is moved axially through the graft 712 and thereby reverts the graft 712 back to its original orientation with the circumferential surface 718 facing inwardly and the circumferential surface 719 facing outwardly. The assembly 700 differs, however, from the assembly 600 in its post-deployment configuration. In particular, the axial space between the connected ends 714 and 724 results in the connected ends 724 of the stent 720 projecting axially beyond the connected end 714 of the graft 712. Hence, the stent 720 can be in face-to-face engagement with the inner circumferential surface of the blood vessel. Such direct affixation between the stent 720 and the blood vessel may, in some instances, achieve better affixation than a graft-to-blood vessel affixation. The relative positions of the free ends 716 and 722 of the graft 712 and stent 720 respectively can take any of the optional orientations depicted in FIG. 29 and described with respect to the previous embodiment.

The aspect of the invention described with respect to FIGS. 25-46 also can be applied to a bifurcated graft as illustrated in FIGS. 48-53. In particular, FIG. 43 shows a bifurcated graft 812 having a primary leg 813 with a primary end 814. Additionally, the graft 812 has first and second bifurcated legs 815-1 and 815-2 respectively. The first bifurcated leg 815-1 has an end 816-1 and the second bifurcated leg 815-2 has an end 816-2. The graft 812, in the FIG. 48 orientation, further has an inner circumferential surface 818 and an outer circumferential surface 819.

Figure 49:
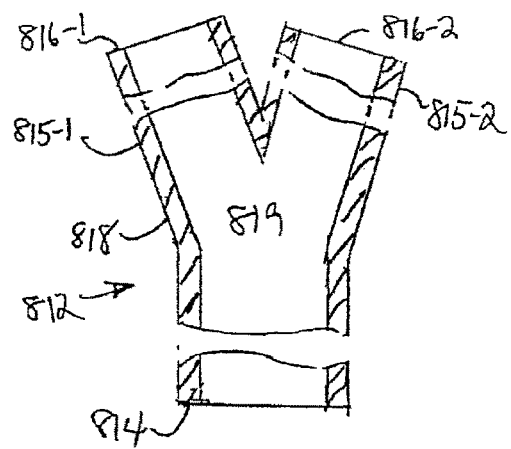
FIG. 49 shows the graft of FIG. 48 in an inside out inverted orientation.

The graft 812 then is turned inside out and into the orientation shown in FIG. 49. This is roughly comparable to the inversion described above with respect to FIG. 26 and is roughly comparable to turning a pair of pants completely inside out. As a result, the initial inner circumferential surface 818 faces outwardly and the initial outer circumferential surface 819 faces inwardly.

Figure 50:
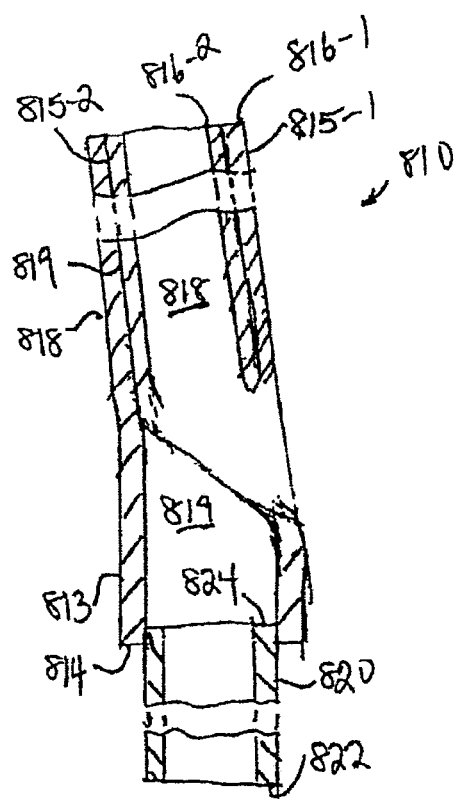
FIG. 50 is a schematic view of the inverted graft of FIG. 49 with one leg of the bifurcated graft folded into the other and with a stent connected in substantially end-to-end relationship with the graft to define a deployment orientation.

The graft 812 then is manipulated further by folding and inverting the second leg 815-2 to lie substantially completely within the first leg 815-1. This is roughly comparable to folding the inverted pair of pants so that one leg lies completely within the other leg. In this configuration, the second leg 815-2 is returned temporarily to its initial orientation with the circumferential surface 818 facing inwardly and with the circumferential surface 819 facing outwardly. Other parts of the bifurcated graft 812, however, retain the orientation shown in FIG. 49. FIG. 50 further shows a stent 820 with a free end 822 and a connected end 824. The connected end 824 is joined substantially in end-to-end relationship with the primary end 814 of the graft 812.

The assembly 810 can be deployed substantially as described with respect to the embodiment of FIGS. 25-41. More particularly, the assembly 810 is disposed in an introducer sheath by releasably affixing the ends 816-1, 816-2 of the bifurcated legs 815-1, 815-2 near the leading end of the introducer sheath. As described above, the releasable attachment may be achieved by sutures or other known attachment means.

Figure 47:
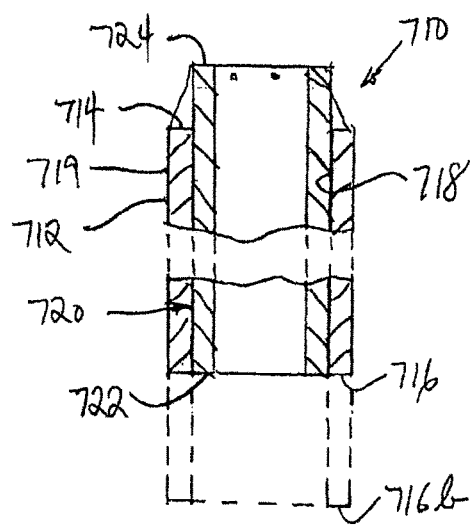
FIG. 47 is schematic view of the eighteenth embodiment after deployment.
Figure 48:
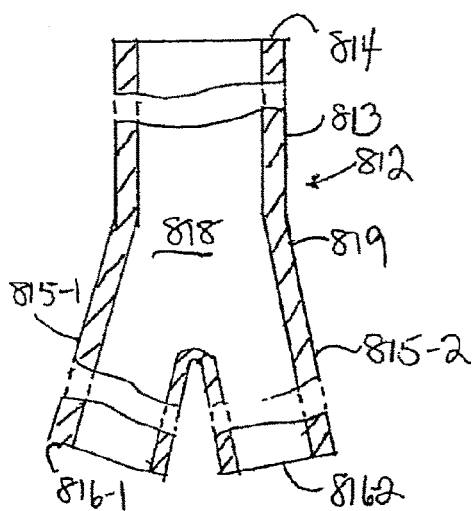
FIG. 48 is schematic view of a graft for use in nineteenth embodiment of the invention showing the graft in an initial orientation that corresponds to a post-deployment orientation.
Figure 51:
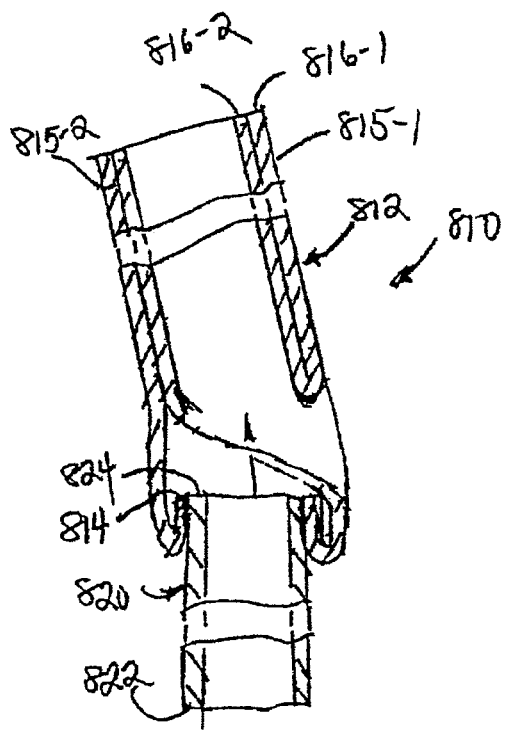
FIG. 51 is a schematic view of the stent/graft assembly of FIG. 50 at a second stage during deployment.
Figure 52:
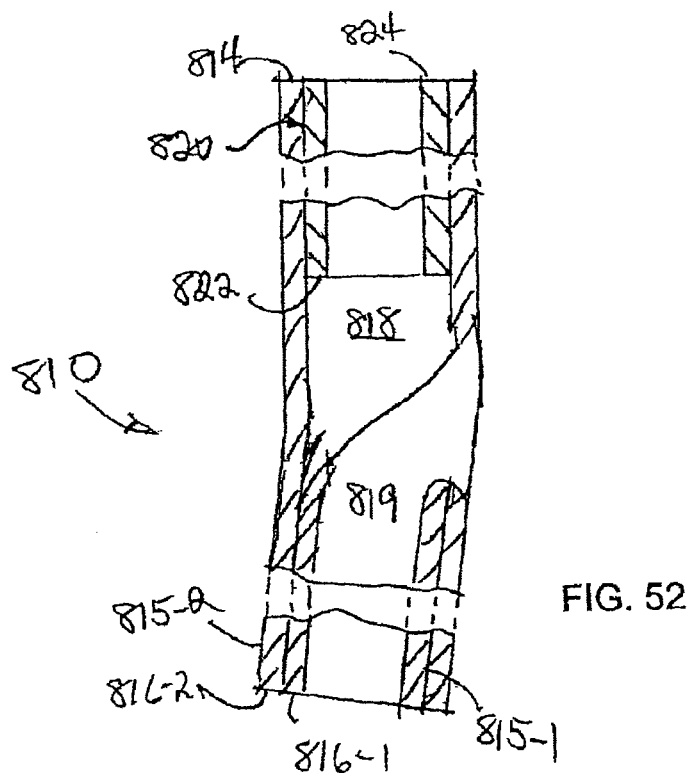
FIG. 52 is a schematic view of the stent/graft assembly of FIGS. 50 and 51 in a third stage of deployment.
Figure 53:
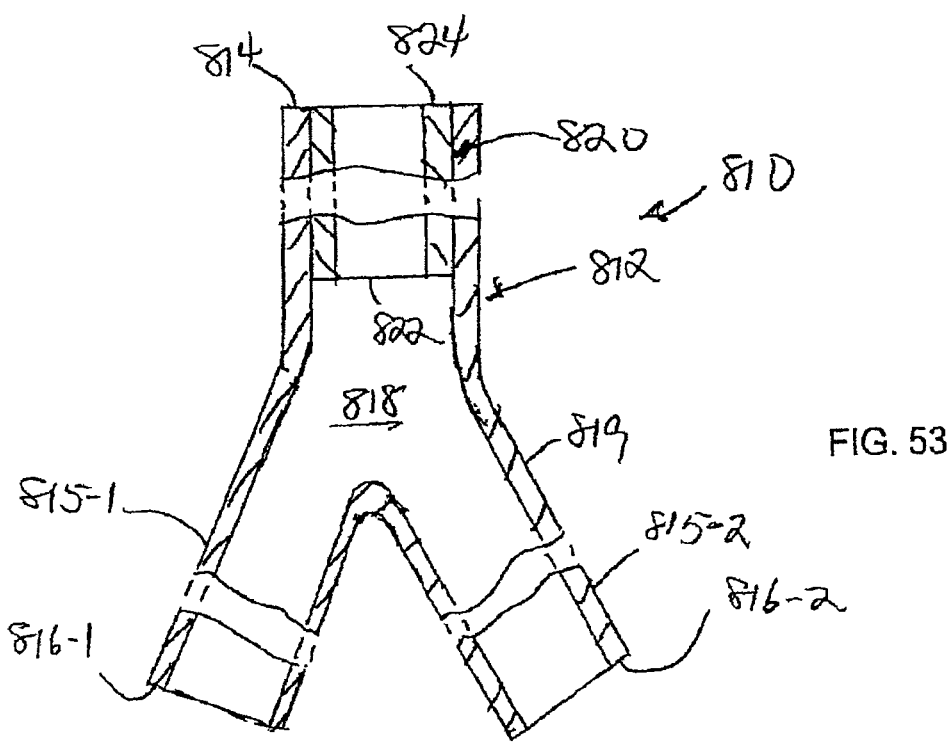
FIG. 53 is a schematic view of the stent/graft assembly of FIGS. 50-52 after complete deployment.

The assembly 810 is deployed to a proper position by the introducer sheath. The stent 820 then is moved axially within the graft 812 substantially as shown in FIG. 51. This movement of the stent 820 causes a gradual inversion of the graft 812 substantially as described with the embodiment of FIGS. 25-29. However, in this embodiment the stent 820 moves axially within the telescoped bifurcated legs 815-1 and 815-2. The advancement of the stent 820 axially within the graft 812 terminates when the connected end 824 of the stent 820 is positioned properly with respect to the connected primary end 814 of the graft 812. In the embodiment of FIG. 52 the connected ends 814 and 824 are substantially registered. However, the stent 820 may extend axially beyond the connected end 814 of the graft 812 substantially as described with respect to the embodiments of FIGS. 46 and 47. FIG. 52 shows the stent 820 in one possible final position relative to the primary leg 813 of the bifurcated graft 812. In the FIG. 53 orientation, however, the graft 812 has completely inverted from the orientation shown in FIG. 50. Thus, the circumferential surface 818 faces inwardly on most of the graft and the circumferential surface 819 faces outwardly on most of the graft. However, the second bifurcated leg 815-2 is still folded into the first bifurcated leg 815-1. Additionally, the second bifurcated leg 815-2 has returned again its inverted orientation with the circumferential surface 818 facing outwardly thereon and the circumferential surface 819 facing inwardly thereon.

Deployment of the assembly 810 is completed by returning the second bifurcated leg 815-2 to its final position outside of the first bifurcated leg 815-1. Thus, the circumferential surface 818 faces inwardly throughout the bifurcated graft 812 and the circumferential surface 819 faces outwardly on the entire bifurcated graft 812. In this final deployed position, the first and second bifurcated legs 815-1 and 815-2 may be in the femoral arteries of the patient.

As with the preceding embodiments, the assembly 810 provides a desirably small cross section for deployment while avoiding the need for a subsequent deployment of an internal stent on the main leg 813 of the bifurcated graft 812. Internal stents may be required in their respective bifurcated legs 815-1 and 815-2. However, the entire surgical procedure is simplified.

Figure 54:
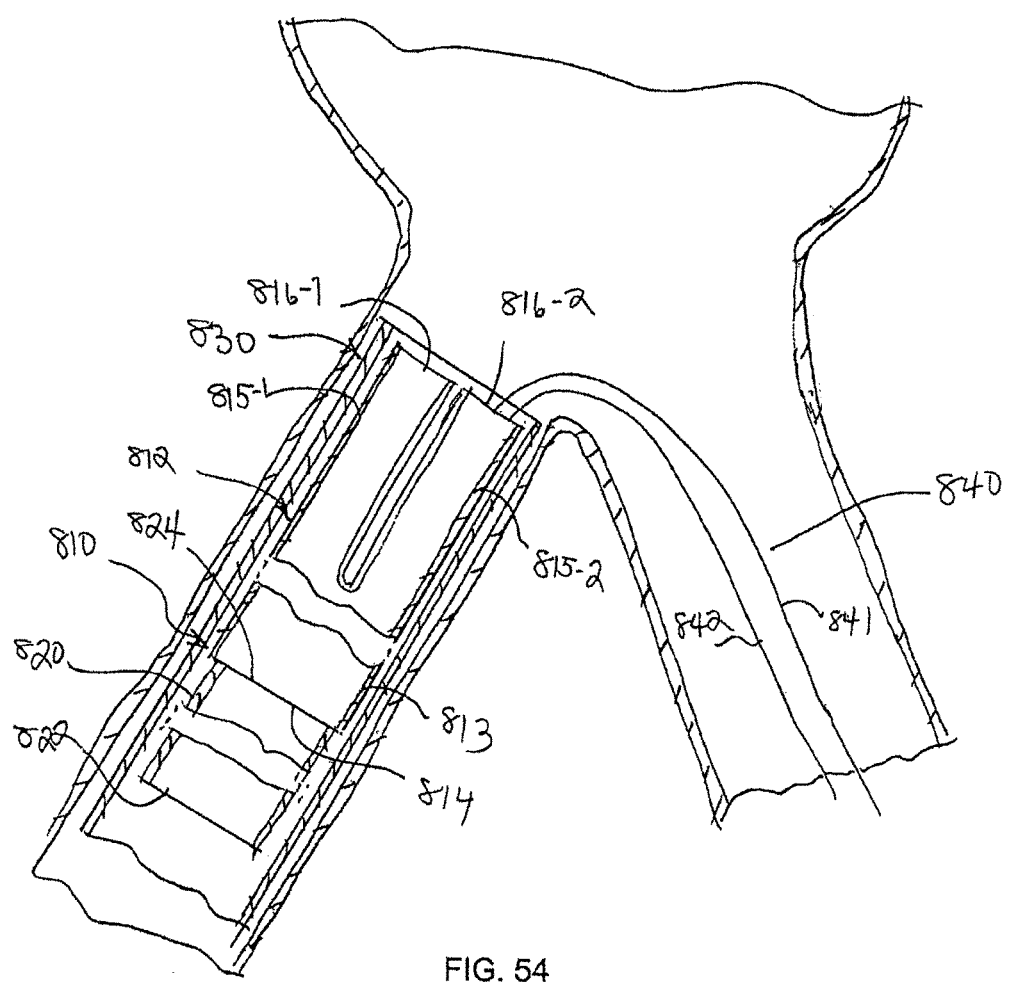
FIG. 54-56 are schematic views showing an alternate way of deploying the stent/graft assembly that is depicted in FIGS. 48-53.
Figure 55:
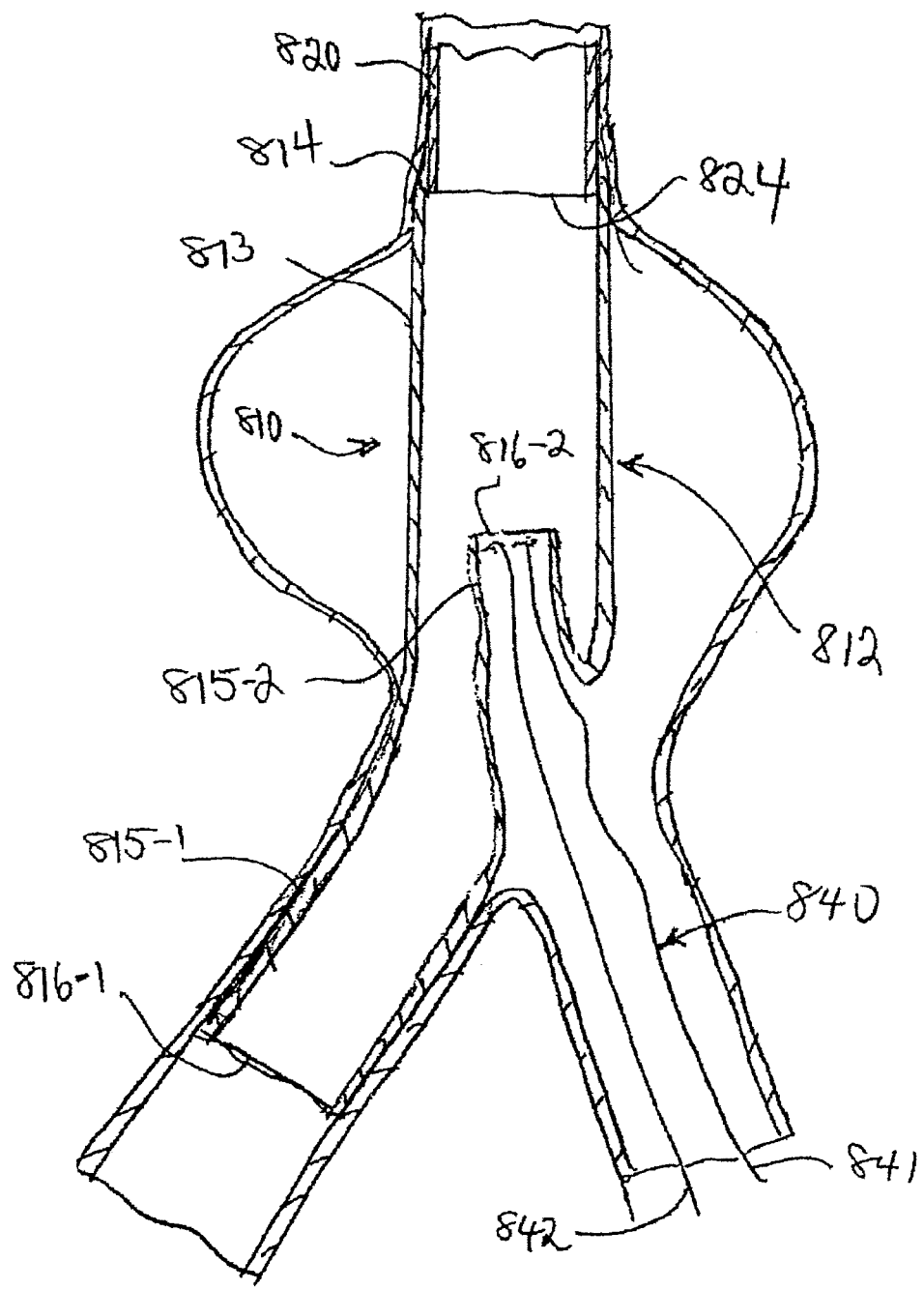
Figure 56:
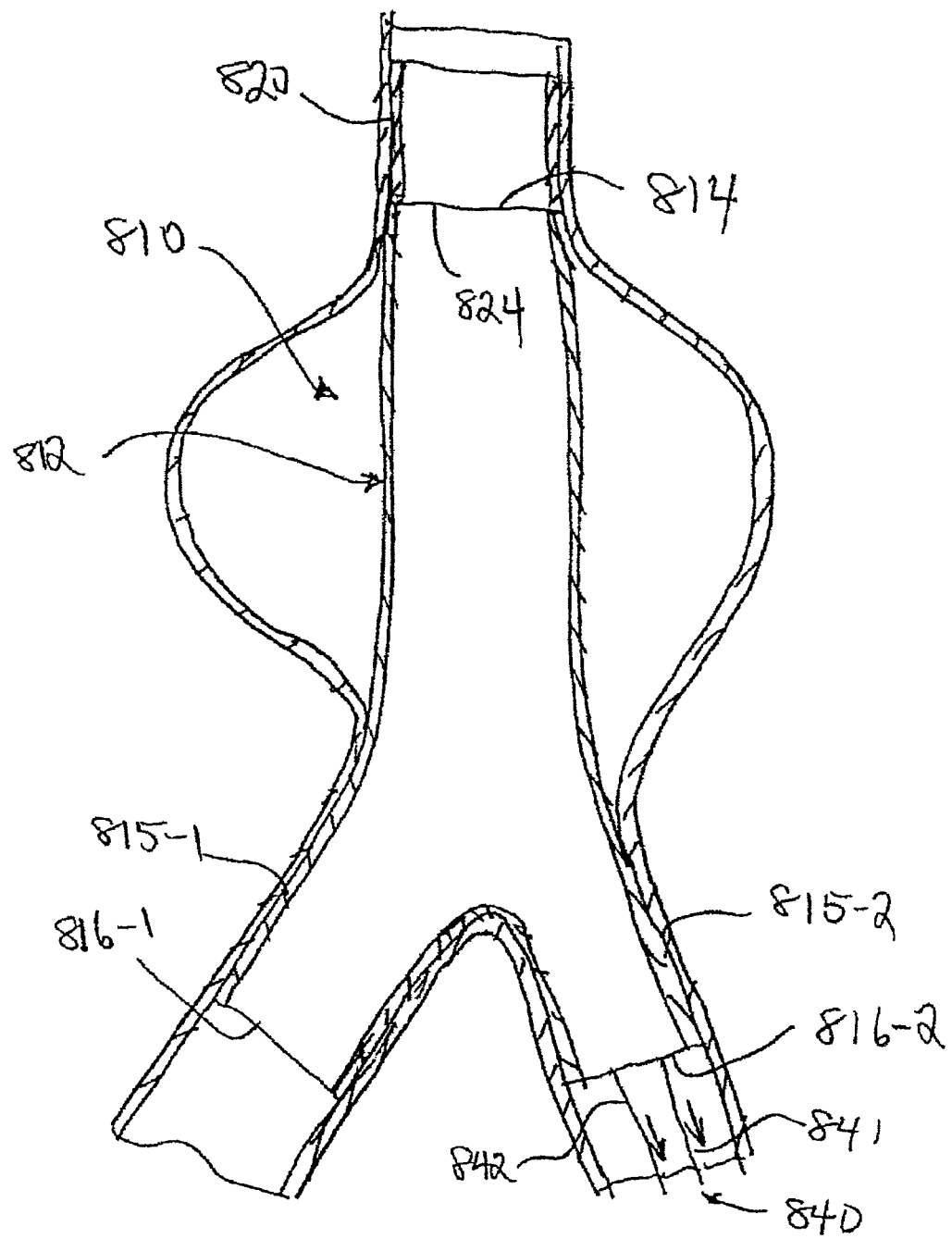

FIGS. 54-56 show an optional method for deploying the stent/graft assembly 810. In particular, the graft 812 is completely inverted from the FIG. 48 orientation into the FIG. 49 orientation and the connected end 824 of the stent 820 is secured in substantially end-to-end relationship with the end 814 of the graft 812. In the embodiment of FIGS. 48-53, the second leg 815-2 is inverted and inserted into the first leg 815-1. In this embodiment, however, the second leg 815-2 is permitted to collapse, but is not inserted into the first leg. The two collapsed legs are inserted into introducer sheath 830 so that the graft 812 is in a leading position relative to the stent 820. The introducer sheath 830 then may be used to guide the assembly 810 into an appropriate position in the femoral artery of the ipsilateral limb. The stent 820 then is pushed into the first bifurcated leg 815-1 of the graft 812 and thereby turns the main leg 813 and the first bifurcated leg 815-1 inside out. This process will loosely position the second bifurcated leg 815-2 in an inverted orientation inside the main leg 813 and/or the first bifurcated leg 815-1. The second bifurcated leg 815-2 then is turned inside out and positioned properly within the femoral artery of the contrailateral limb.

The movement of the second femoral leg 815-2 can be achieved by pull suture assembly 840. In this regard, a pull suture assembly 840 is considered to define two sutures 841, 842 that are stitched together onto the second bifurcated leg 815-2 in such a manner that a pulling force on both sutures of the pull suture assembly 840 will permit the pulling force to be transmitted to the portion of the graft 812 into which the sutures 841, 842 are sewn. However, a pulling force on only one of the sutures 841 or 842 will permit the two sutures 841, 842 to separate from one another and from the graft. Thus, the two sutures can be pulled simultaneously to deploy the second bifurcated leg 815-2 properly. However, a single suture may then be pulled to separate the sutures from the graft 812.

While the invention has been described with respect to certain preferred embodiments, it is apparent that various changes can be made without departing from the scope of the invention as defined by the appended claims. For example, for each of the optional embodiments, and variations thereof, the substantially end-to-end stent-to-graft connections can be pure end-to-end abutment as depicted schematically in FIG. 2 or a slightly overlapped telescoped arrangement, as shown in FIG. 3. In other options, there may be a greater telescoping between the graft and stent prior to deployment and/or during deployment. However, the graft and stent then may be extended intraoperatively into the slightly overlapped relationship depicted in FIG. 3. Embodiments of the invention that show a curved stent/graft assembly with the stent and the graft substantially coextensive may comprise a single tubular graft with a plurality of stents disposed substantially in end-to-end relationship with one another or in axially spaced relationship to one another. At least certain of the stents may comprise a single ring or a short section of a helix. In these embodiments, the graft may be inside the one or more stents, outside the one or more stents or the assembly may have two tubular grafts disposed respectively inside and outside the one or more stents. Additionally, as noted above, at least a portion of a graft connected in end-to-end relationship with a stent may be connected preoperatively to its own stent. This later embodiment would not achieve a minimum cross-sectional dimension with a correspondingly easier insertion, but may achieve a more secure affixation than assemblies that rely upon only a coaxially coextensive stent and graft.

The temporary connection between the graft and the introducer sheath can take forms other than the sutures specifically mentioned above. These connections may include a weak adhesive bond, a cohesion or a temporary retention between hook like structures and loops.

A tubular introducer sheath has been depicted in the figures. However, other introducing mechanisms can be employed, such as a simple introducer wire or a plurality of wires. Similarly, the means for moving the contralateral leg of the bifurcated graft internally through the inverted graft can be carried out by any of a plurality of known means, including the use a second introducer sheath, an additional wire or a pull thread.

The introducer sheath is depicted schematically as a continuous tube. However the end of the introducer sheath may have slits, perforations or other expandable regions to facilitate movement of the stent through the sheath.

What is claimed is:

1. An endovascular stent/graft assembly for repairing a section of a blood vessel that has an aneurysm, the blood vessel having first and second relatively healthy sections adjacent and on opposite ends of the aneurysm, the assembly comprising:
   a tubular stent configured to directly contact a first relatively healthy section of the blood vessel, the stent having opposite first and second axial ends;
   a tubular graft having a first axial end, a second axial end, a tubular portion adjacent the first axial end configured to directly contact the first relatively healthy section of the blood vessel, and a flexible wall between the first and second axial ends of the graft, substantially the entirety of the graft being unsupported by any framework;
   a discrete ring attached to the graft in proximity to the first axial end of the graft and configured to keep the graft open when in the blood vessel and without encircling the tubular stent, the discrete ring not being a component of the tubular stent; and
   a plurality of axially projecting extensions comprising wires or hooks extending from the discrete ring beyond the first axial end of the graft and connected to the second axial end of the stent, the plurality of axially projecting extensions comprising wires or hooks mounted at circumferentially spaced apart locations on the discrete ring, each of the plurality of axially projecting extensions comprising a radially extending connecting surface remote from its respective mounting location for connecting the stent to the discrete ring and achieving an immediately adjacent end-to-end axial connection between the second axial end of the stent and the first axial end of the graft without overlap between the stent and the graft;
   wherein the immediately adjacent end-to-end axial connection without overlap is a non-abutting connection defining a small axial gap between the second axial end of the stent and the first axial end of the graft;
   wherein the immediately adjacent end-to-end axial connection without overlap enables a smaller cross-section than an end-to-end axial connection with overlap so that the assembly can be introduced more easily into the blood vessel; and
   wherein the stent is connected to the graft via said plurality of axially projecting extensions comprising wires or hooks.

2. The endovascular stent/graft assembly of claim 1, wherein at least one of the radially extending connecting surfaces comprises a barb or a hook.

3. The endovascular stent/graft assembly of claim 1, wherein the radially extending connecting surfaces are releasable.

4. The endovascular stent/graft assembly of claim 1, wherein each of the plurality of axially projecting extensions is connected at its respective circumferential location by a fuse, adhesive, or weld.

5. An endovascular stent/graft assembly for repairing a section of a blood vessel that has an aneurysm, the blood vessel having first and second relatively healthy sections adjacent and on opposite ends of the aneurysm, the assembly comprising:
   a substantially tubular stent having opposite first and second axial ends and configured to directly contact a first relatively healthy section of the blood vessel,
   a tubular graft having first axial and second axial ends and a flexible wall portion therebetween, substantially the entirety of the graft being unsupported by any framework;
   a discrete annular member affixed to the graft in proximity to its first axial end and configured to keep the graft open during deployment without encircling the stent, the discrete annular member not being a component of the tubular stent;
   a plurality of axially extending wires projecting beyond the first axial end of the graft from the annular member toward the the second axial end of the stent, the plurality of axially extending wires mounted at a plurality of circumferentially spaced apart locations on the discrete annular member; and
   a hook having a curved or angular surface projecting radially from a distal portion of each axially extending wire and configured to connect the annular member and the second axial end of the stent at the plurality of circumferentially spaced apart locations to maintain an immediately adjacent end-to-end axial non-abutting connection without overlap between the stent and the graft;

wherein the immediately adjacent end-to-end axial non-abutting connection without overlap defines a small axial gap between the second axial end of the stent and the first axial end of the graft;

wherein the connection without overlap enables a smaller cross-section than a connection with overlap so that the assembly can be introduced more easily into the blood vessel; and wherein the stent is connected to the graft via said plurality of axially extending wires.

6. The endovascular stent/graft assembly of claim 5, wherein the plurality of axially extending wires is fused, welded, adhered or bonded to the stent or to the annular member.

7. The endovascular stent/graft assembly of claim 6, wherein at least one of the axially extending wires is fused, welded, adhered or bonded to the annular member.

8. The assembly of claim 5, wherein the annular member comprises is a discrete ring affixed to the graft.

9. The endovascular stent/graft assembly of claim 5, wherein the plurality of axially extending wires are disposed at least partially in the gap between the stent and the graft.

\* \* \* \* \*